United States Patent
Morita et al.

(10) Patent No.: US 11,924,196 B2
(45) Date of Patent: Mar. 5, 2024

(54) COMMUNICATION TERMINAL AND POSITION DETECTION SYSTEM

(71) Applicant: KONICA MINOLTA, INC., Tokyo (JP)

(72) Inventors: Akemi Morita, Nara (JP); Yutaka Yasunaga, Hachioji (JP); Shinya Hashimoto, Nishinomiya (JP)

(73) Assignee: KONICA MINOLTA, INC., Tokyo (JP)

( * ) Notice: Subject to any disclaimer, the term of this patent is extended or adjusted under 35 U.S.C. 154(b) by 390 days.

(21) Appl. No.: 17/220,070

(22) Filed: Apr. 1, 2021

(65) Prior Publication Data

US 2021/0344665 A1 Nov. 4, 2021

(30) Foreign Application Priority Data

Apr. 30, 2020 (JP) ................................ 2020-080277
Sep. 1, 2020 (JP) ................................ 2020-146571

(51) Int. Cl.
*H04L 9/40* (2022.01)
*G06F 1/16* (2006.01)
*G06K 19/07* (2006.01)

(52) U.S. Cl.
CPC ............ *H04L 63/083* (2013.01); *G06F 1/163* (2013.01); *G06K 19/0723* (2013.01)

(58) Field of Classification Search
CPC ... H04L 63/083; H04L 63/0823; G06F 1/163; G06F 21/32; G06K 19/0723; A61B 2562/08; H04W 12/06; H04W 12/08; H04W 12/33
See application file for complete search history.

(56) References Cited

U.S. PATENT DOCUMENTS

| | | | |
|---|---|---|---|
| 2015/0180866 A1 | 6/2015 | Hama | |
| 2015/0342524 A1* | 12/2015 | Sudo | G16H 15/00 340/870.07 |
| 2023/0126114 A1* | 4/2023 | Akutsu | G06F 3/04883 382/118 |

FOREIGN PATENT DOCUMENTS

| | | |
|---|---|---|
| CN | 101335470 A | 12/2008 |
| CN | 108733998 A | 11/2018 |
| JP | 2006-048470 A | 2/2006 |
| JP | 2008541244 A | 11/2008 |

(Continued)

OTHER PUBLICATIONS

Notification of the First Office Action issued in Chinese Patent Application No. 202110474757.4, dated Feb. 17, 2023, with English Translation (24 pages).

(Continued)

*Primary Examiner* — Izunna Okeke
(74) *Attorney, Agent, or Firm* — BUCHANAN INGERSOLL & ROONEY PC

(57) ABSTRACT

A communication terminal includes a memory in which identification information associated with a user is stored, a controller that carries out authentication of the user, and a communication interface that transmits a signal including the identification information. When user authentication is successful, the controller sets the communication terminal to a first state in which the signal is transmitted to an external apparatus, and when user authentication is not successful, the controller sets the communication terminal to a second state in which the signal is not transmitted to the external apparatus.

28 Claims, 24 Drawing Sheets

(56) References Cited

FOREIGN PATENT DOCUMENTS

| | | |
|---|---|---|
| JP | 2015-121904 A | 7/2015 |
| WO | 2019/017440 A1 | 1/2019 |

OTHER PUBLICATIONS

Office Action (Notice of Reasons for Refusal) dated Nov. 7, 2023, by the Japan Patent Office in corresponding Japanese Patent Application No. 2020-080277 and an English translation of the Office Action. (12 pages).

Office Action (Notice of Reasons for Refusal) dated Dec. 5, 2023, by the Japan Patent Office in corresponding Japanese Patent Application No. 2020-146571 and an English translation of the Office Action. (12 pages).

\* cited by examiner

COMMUNICATION TERMINAL AND POSITION DETECTION SYSTEM

The entire disclosure of Japanese Patent Applications Nos. 2020-080277 and 2020-146571 filed on Apr. 30 and Sep. 1, 2020, respectively, is incorporated herein by reference in its entirety.

BACKGROUND

Technological Field

The present disclosure relates to a communication terminal carried by a user and a system that detects a position of a user by using the communication terminal.

Description of the Related Art

A communication terminal that provides identification information such as a radio frequency (RF) tag has conventionally been used for detecting a position of a human or an object. For example, Japanese National Patent Publication No. 2008-541244 discloses a technique for detecting a position of an individual by providing the individual with clothing embedded with an RFID tag and detecting a position of the RFID tag containing the identification information.

SUMMARY

The technique disclosed in Japanese National Patent Publication No. 2008-541244 does not discuss whether or not an intended user is wearing the RFID tag. In general, for specifying whether or not an individual is an intended individual, an authentication technique is used. Examples of such an authentication technique include authentication by entry of an ID or a password and biometric authentication using fingerprints or the like. Therefore, reliability in determining a specified position as the position of the intended individual may be improved by adding an authentication unit to an RF tag and linking a result of authentication to identification information in the RF tag.

Even though the RF tag is linked to a user at a certain time point, however, after authentication, the RF tag may be handed to somebody else, may be lost and picked up by another user, or may be stolen. In that case, such a fact cannot be detected based on data alone, and a position of a user different from the user who should have originally been specified is detected based on the RF tag.

Under the circumstances described above, a technique for improving reliability of a result of detection by a position detection system has been demanded.

To achieve at least one of the abovementioned objects, according to an aspect of the present invention, a communication terminal reflecting one aspect of the present invention comprises a memory in which identification information associated with a user is stored, a controller that carries out authentication of the user, and a communication interface that transmits a signal including the identification information. When authentication of the user is successful, the controller sets the communication terminal to a first state in which the signal is transmitted to an external apparatus, and when authentication of the user is not successful, the controller sets the communication terminal to a second state in which the signal is not transmitted to the external apparatus.

To achieve at least one of the abovementioned objects, according to another aspect of the present invention, a communication terminal reflecting another aspect of the present invention comprises a memory in which identification information associated with a user is stored, a controller that obtains a result of authentication of the user from a device that carries out user authentication, and a communication interface that transmits a signal including the identification information. When user authentication is not successful, the controller prevents transmission of the signal by the communication interface, and when user authentication is successful, the controller does not prevent transmission of the signal by the communication interface.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention.

DETAILED DESCRIPTION OF EMBODIMENTS

Figure 1:
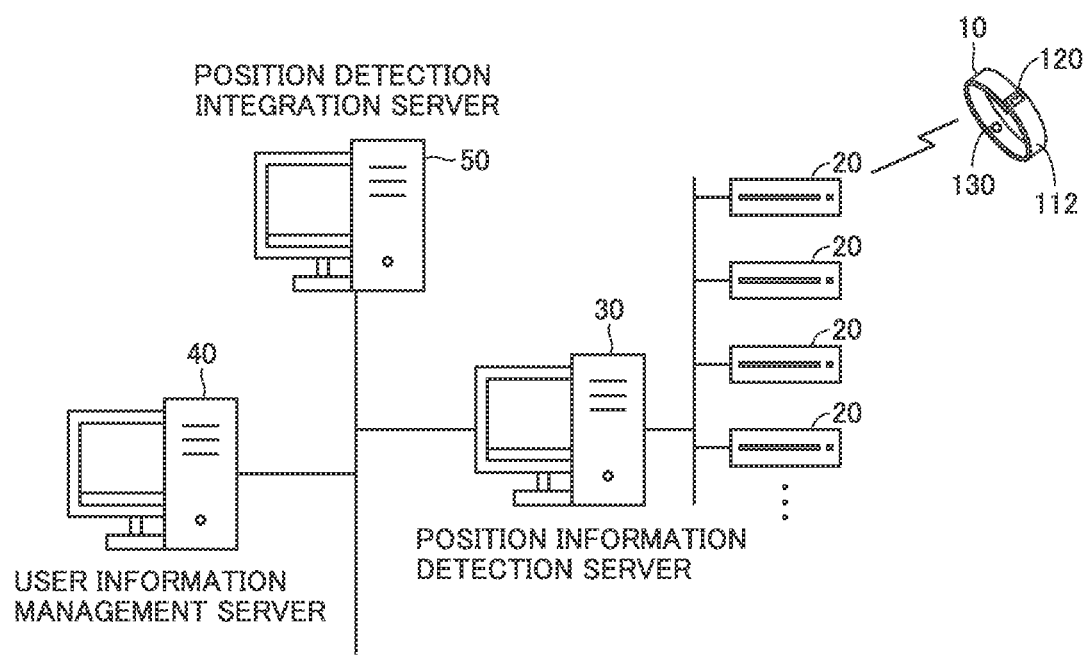
FIG. 1 is a diagram showing an exemplary configuration in a first embodiment of a position detection system.

Hereinafter, one or more embodiments of the present invention will be described with reference to the drawings. However, the scope of the invention is not limited to the disclosed embodiments.

An embodiment of a position detection system will be described below with reference to the drawings. The same elements and components in the description below have the same reference characters allotted and their labels and functions are also the same. Therefore, description thereof will not be repeated.

First Embodiment

[1. Configuration of Position Detection System]

FIG. 1 is a diagram showing an exemplary configuration in a first embodiment of a position detection system.

As shown in FIG. 1, the position detection system includes an authentication terminal 10, an RFID reader 20, a position information detection server 30, a user information management server 40, and a position detection integration server 50.

The position detection system can include at least two authentication terminals 10. Authentication terminal 10 represents an exemplary communication terminal and transmits a signal including information (a terminal ID) for identifying authentication terminal 10.

Authentication terminal 10 includes a belt 112. A user can thus wear authentication terminal 10 on the user's body. Though authentication terminal 10 is implemented by a wearable terminal in the first embodiment, the authentication terminal does not necessarily have to include a feature for being attached to the user's body. Authentication terminal 10 may be implemented by a terminal such as a smartphone in which an application program for performing a function as described herein is installed.

Authentication terminal 10 includes a first sensor 120 (for example, a fingerprint sensor) used for user authentication and a second sensor 130 (for example, a body temperature sensor) used for detection of continuation of wearing of authentication terminal 10 by the user. Details of a configuration of authentication terminal 10 will be described later with reference to FIG. 3 or the like.

The position detection system can include at least two RFID readers 20. When each RFID reader 20 receives a signal from authentication terminal 10, it transmits, in association with each other, information (RFID) for identifying each RFID reader 20 and a terminal ID included in the signal to position information detection server 30. RFID reader 20 may further transmit information for specifying time of reception of the signal from authentication terminal 10 to position information detection server 30.

Position information detection server 30 transmits the information received from each RFID reader 20 to position detection integration server 50.

User information management server 40 manages information (a user database) in which each of at least two user names is associated with a terminal ID of each of the at least two authentication terminals 10 on one-to-one basis. User information management server 40 transmits the user database to position detection integration server 50.

As set forth above, position detection integration server 50 obtains a terminal ID associated with an RFID from position information detection server 30 and obtains the user database (a user name associated with each terminal ID) from user information management server 40.

By referring to the user database, position detection integration server 50 obtains a user ID associated with a terminal ID associated with an RFID obtained from position information detection server 30. A user name of a user located within coverage of each RFID reader 20 can thus be specified.

Authentication terminal 10 transmits a signal when user authentication in authentication terminal 10 is successful. Therefore, authentication terminal 10 can transmit the signal on condition that it is carried by an authenticated user.

[2. Exemplary Use of Position Detection System]

Figure 2:
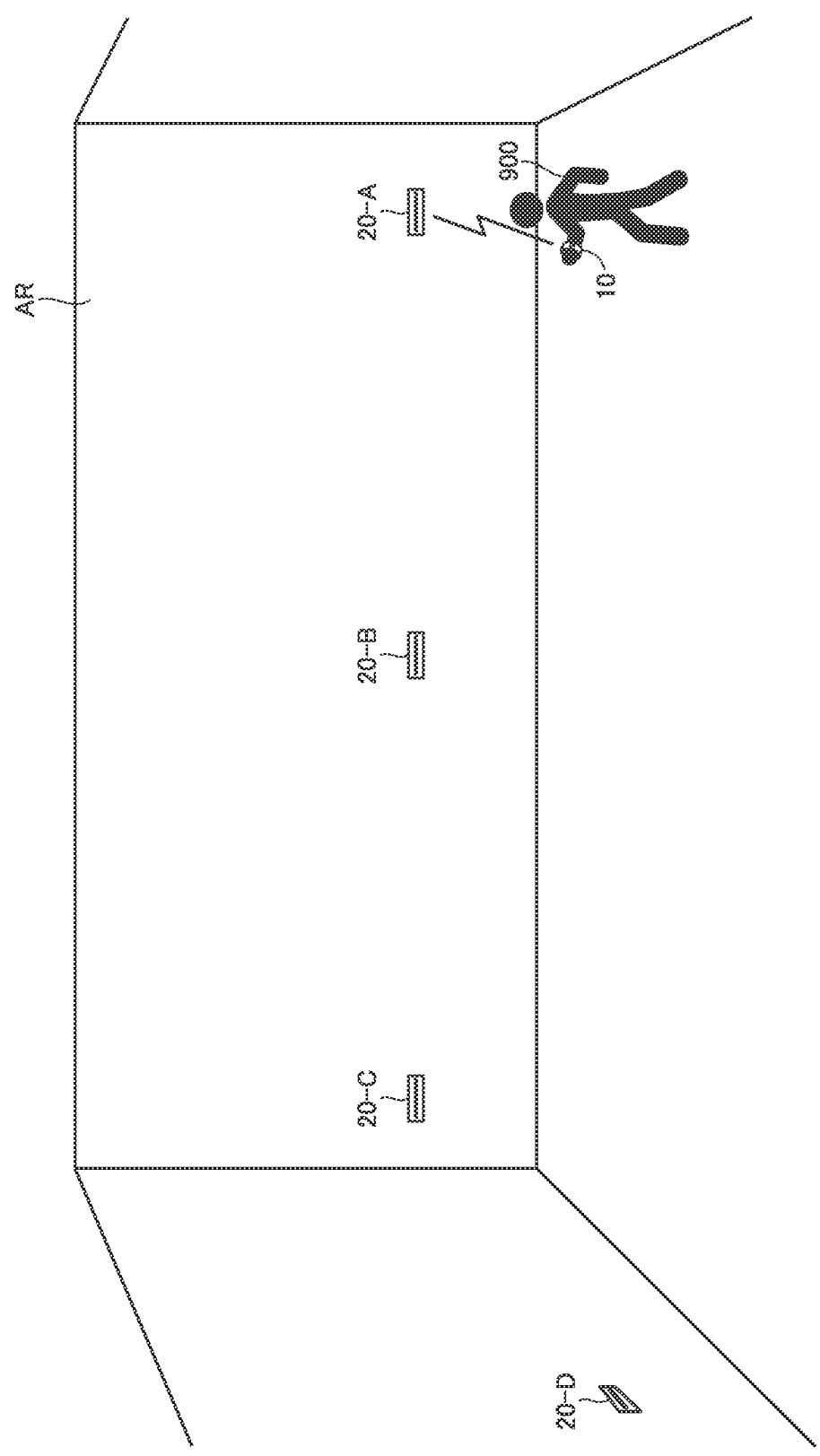
FIG. 2 is a diagram showing an exemplary scene where the position detection system is used.

FIG. 2 is a diagram showing an exemplary scene where the position detection system is used. In the example in FIG. 2, a user 900 wears authentication terminal 10 on his/her arm.

In the example in FIG. 2, an area where a position of a user is to be detected is shown as an area AR. RFID reader 20 is provided at each of a plurality of locations within area AR. In FIG. 2, RFID readers 20 are provided with references (20-A, 20-B, 20-C, and 20-D) different from one another.

Ina state shown in FIG. 2, user 900 is located in the vicinity of RFID reader 20-A. When authentication terminal 10 successfully authenticates user 900, it transmits a signal including a terminal ID of authentication terminal 10. RFID reader 20-A receives the signal and transmits the signal to position information detection server 30 together with an ID of RFID reader 20-A. Position information detection server 30 transmits the received signal to position detection integration server 50, and position detection integration server 50 uses the signal received from position information detection server 30 to specify that user 900 is located in the vicinity of RFID reader 20-A.

As shown in FIG. 2, the position detection system can be used, for example, to specify which user is located in a security area or to generate records of positions of one user, however, these are merely exemplary methods of use of the position detection system.

[3. Hardware Configuration]

Figure 3:
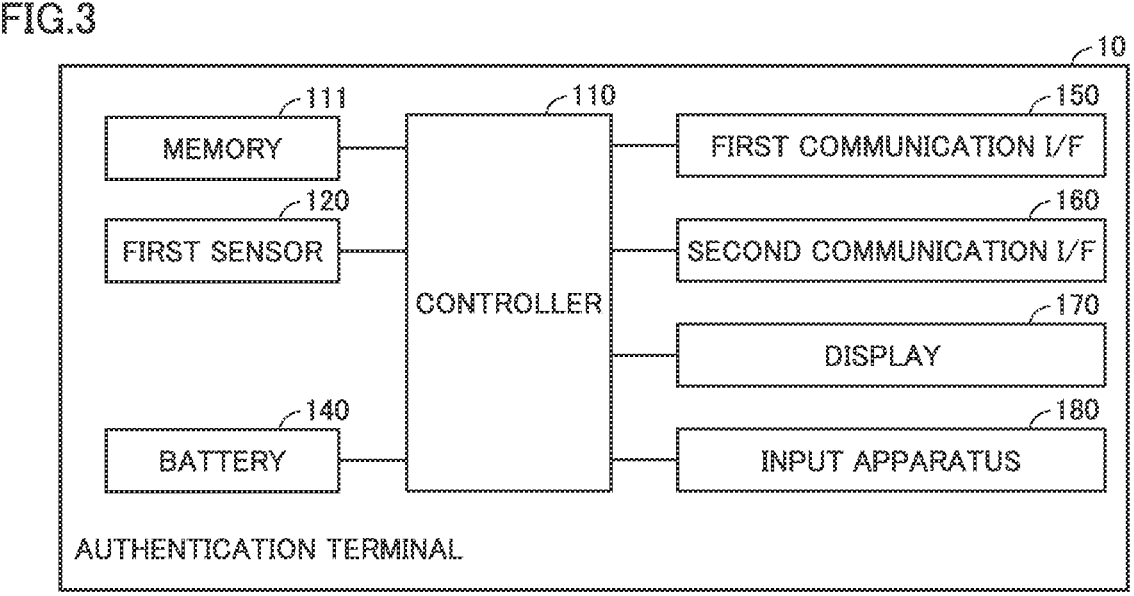
FIG. 3 is a diagram showing an exemplary hardware block of an authentication terminal 10.

FIG. 3 is a diagram showing an exemplary hardware block of authentication terminal 10. As shown in FIG. 3, authentication terminal 10 includes a controller 110, a memory 111, a first sensor 120, a battery 140, a first communication I/F 150, a second communication I/F 160, a display 170, and an input apparatus 180.

Controller 110 controls operations of authentication terminal 10. In one implementation, controller 110 includes a central processing unit (CPU), and controller 110 controls operations of authentication terminal 10 by having the CPU execute a given program. In another implementation, controller 110 includes a control circuit (an application specific integrated circuit (ASIC), a field-programmable gate array (FPGA), etc.) and controls operations of authentication terminal 10 based on operations of these circuits.

Various types of data to be used for controlling authentication terminal 10 are stored in memory 111.

First sensor 120 is used for detecting data such as biometric information when authentication terminal 10 requires detection of such data for user authentication. For example, authentication terminal 10 may authenticate a user by heart rate pattern authentication, and in this case, first sensor 120 can be implemented by a heart rate sensor. Alternatively, authentication terminal 10 may authenticate a user based on a vein pattern in a wrist or a finger, and in this case, first sensor 120 can be implemented by a near infrared sensor.

Battery 140 can be implemented by batteries of various forms, and can supply electric power to various elements within authentication terminal 10.

First communication I/F 150 is a communication interface (an interface may also be denoted as "I/F") that transmits radio waves for authentication terminal 10 to function as an active RFID tag.

Second communication I/F 160 is an interface for data communication through wireless LAN or Bluetooth®, and implemented, for example, by a wireless module in conformity with Institute of Electrical and Electronics Engineers (IEEE) 802.15.4 or an interface for Bluetooth® communication.

Display 170 shows a state of authentication terminal 10. Display 170 may be implemented by a display unit such as a liquid crystal display, an element such as a light emitting diode (LED), or combination thereof.

Input apparatus 180 accepts input of information into authentication terminal 10. Input apparatus 180 may be implemented by a hardware key, a software key shown on display 170, or combination thereof.

[4. Functional Configuration]

Figure 4:
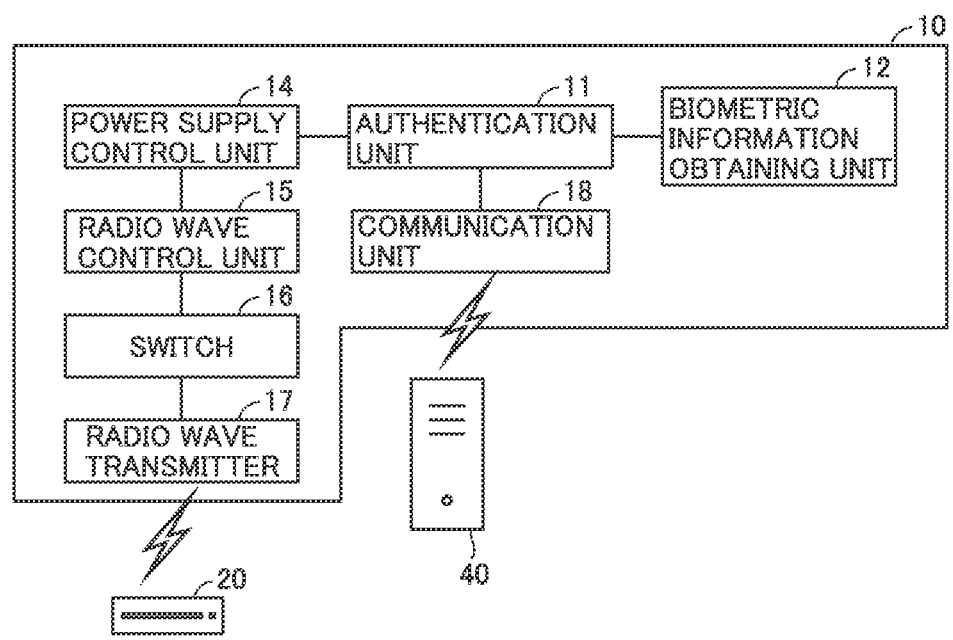
FIG. 4 is a diagram showing an exemplary functional configuration of authentication terminal 10.

FIG. 4 is a diagram showing an exemplary functional configuration of authentication terminal 10. As shown in FIG. 4, authentication terminal 10 includes an authentication unit 11, a biometric information obtaining unit 12, a power supply control unit 14, a radio wave control unit 15, a switch 16, a radio wave transmitter 17, and a communication unit 18 as its functions.

Authentication unit 11 carries out user authentication for confirming that a user who wears authentication terminal 10 is a true user of authentication terminal 10. Authentication unit 11 is implemented by controller 110. Collation information to be used for user authentication is registered in authentication terminal 10, and authentication unit 11 collates information entered for authentication with the collation information and determines whether or not user authentication is successful based on a result of checking.

In one implementation, biometric authentication based on heart rates of a user is carried out as user authentication. In this case, heart rate pattern information of a specific user is registered in advance as the collation information in authentication terminal 10. Authentication unit 11 specifies a degree of matching by checking the entered heart rate information against the heart rate pattern information registered as the collation information. When the degree of matching is equal to or higher than a predetermined threshold value, authentication unit 11 determines user authentication as being successful, and when the degree of matching is lower than the threshold value, authentication unit 11 determines user authentication as having failed.

When authentication unit 11 carries out user authentication based on biometric information, biometric information obtaining unit 12 obtains biometric information for authentication and provides the biometric information to authentication unit 11. Biometric information obtaining unit 12 is implemented by first sensor 120. When authentication unit 11 does not use biometric information for user authentication (for example, when a user is authenticated based on a password), biometric information obtaining unit 12 does not have to be provided, and instead, authentication terminal 10 includes a function to obtain information for authentication such as a password. This function can be performed, for example, by input apparatus 180.

Power supply control unit 14 controls supply of electric power (regulates a voltage) from battery 140 to each element within authentication terminal 10. Power supply control unit 14 is implemented, for example, by an electric circuit included in controller 110.

Radio wave control unit 15 controls radio waves transmitted from authentication terminal 10 that functions as an RFID tag. Radio wave control unit 15 is implemented, for example, by an electric circuit included in controller 110. In one implementation, a terminal ID for identifying authentication terminal 10 is registered in authentication terminal 10. Radio wave control unit 15 includes information for specifying the terminal ID in a signal transmitted by authentication terminal 10 as the RFID tag.

Switch 16 switches between on and off of supply of electric power from battery 140 to radio wave transmitter 17 which will be described later. Switch 16 is implemented, for example, by a switch that physically switches a state of connection (connection/disconnection) between battery 140 and first communication I/F 150. In one implementation, when authentication unit 11 successfully authenticates a user, switch 16 has battery 140 and first communication I/F 150 connected to each other. First communication I/F 150 thus transmits radio waves. When authentication unit 11 has failed in user authentication, switch 16 has first communication I/F 150 disconnected from battery 140. First communication I/F 150 thus does not transmit radio waves.

Radio wave transmitter 17 performs a main function of an RFID tag, and it is implemented, for example, by first communication I/F 150. In one implementation, radio wave transmitter 17 transmits a signal including a terminal ID registered in authentication terminal 10.

In the position detection system in the first embodiment, RFID reader 20 receives radio waves transmitted from radio wave transmitter 17.

Communication unit 18 receives data registered in authentication terminal 10 such as a terminal ID. Communication unit 18 is implemented, for example, by second communication I/F 160, first communication I/F 150, or both of them.

In the position detection system in the first embodiment, communication unit 18 receives data from user information management server 40 over a network. Data such as a terminal ID may be registered in communication unit 18 from an apparatus other than user information management server 40. Data such as a terminal ID may directly be registered in authentication terminal 10 as authentication terminal 10 is operated.

[5. Type of Registered Information]

An exemplary type of information registered in each element of the position detection system will be described.

(1) User Information Management Server 40

A user name, a terminal ID, and collation information are registered in user information management server 40 for each user.

In one implementation, in lending a terminal to each user, a manager of the position detection system registers a user name of each user and a terminal ID in user information management server 40 in association with each other. Each user applies for collation information with the manager. The manager registers the collation information in user information management server 40, further in association with the user name of each user.

(2) Authentication Terminal 10

A terminal ID and collation information are registered in authentication terminal 10.

In one implementation, a terminal ID is registered in authentication terminal 10 at the time of manufacturing thereof. In lending authentication terminal 10 to a user, a manager of the position detection system registers collation information applied for by the user in authentication terminal 10. Authentication terminal 10 in which collation information applied for by the user has been stored is thus lent to the user.

[6. Process Flow]

Figure 5:
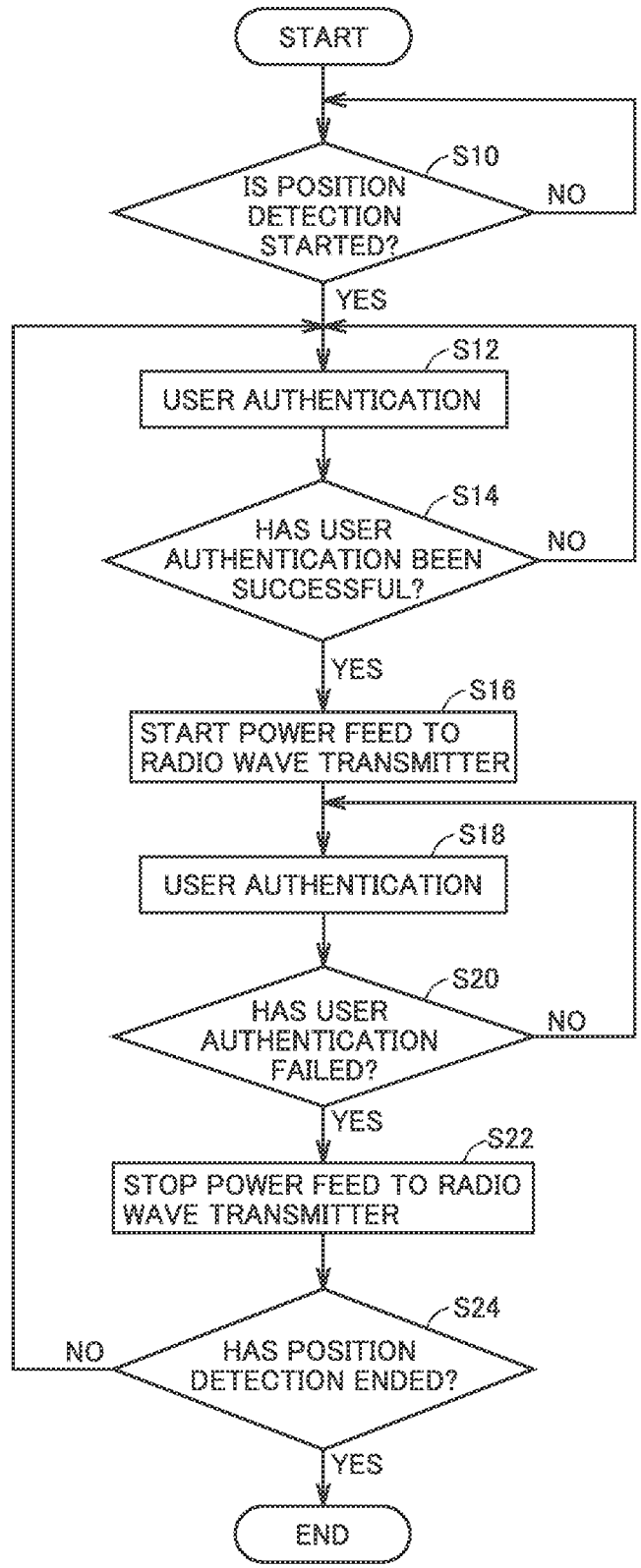
FIG. 5 is a flowchart of exemplary processing performed in authentication terminal 10.

FIG. 5 is a flowchart of exemplary processing performed in authentication terminal 10. Authentication terminal 10 performs a process in FIG. 5, for example, by having a processor of controller 110 execute a given program.

Referring to FIG. 5, in step S10, authentication terminal 10 determines whether or not detection of a position of a user who uses authentication terminal 10 is started. When authentication terminal 10 is configured to be used for position detection simultaneously with start of power on of authentication terminal 10, authentication terminal 10 determines that position detection is started in response to end of start-up processing at the time of power on. When authentication terminal 10 is configured to be used for position detection in response to a prescribed operation, authentication terminal 10 determines that position detection is started in response to the prescribed operation.

When authentication terminal 10 determines that position detection is started (YES in step S10), the process proceeds to step S12, and otherwise (NO in step S10), the process remains in step S10.

In step S12, authentication terminal 10 carries out user authentication. When user authentication is carried out based on biometric information authentication, in step S12, authentication terminal 10 detects heart rates as information for authentication by means of first sensor 120 (the heart rate sensor) and checks the information against a heart rate pattern registered as collation information.

In step S14, authentication terminal 10 determines whether or not a result of authentication in step S12 indicates success. When authentication terminal 10 determines authentication as being successful (YES in step S14), the process proceeds to step S16, and otherwise (NO in step S14), the process returns to step S12.

In step S16, authentication terminal 10 has switch 16 connect first communication I/F 150 to battery 140 and has first communication I/F 150 (radio wave transmitter 17) transmit radio waves including a terminal ID.

In the position detection system, when a user who carries (or wears) authentication terminal 10 is located in area AR (FIG. 2), RFID reader 20 (any one of RFID readers 20-A to 20-D in FIG. 1) located in the vicinity of the user receives the signal transmitted from authentication terminal 10.

In step S18, authentication terminal 10 carries out user authentication as in step S12.

In step S20, authentication terminal 10 determines whether or not user authentication in step S18 has failed. When authentication terminal 10 determines user authentication as having failed (YES in step S20), the process proceeds to step S22, and otherwise (NO in step S20), the process returns to step S18.

In step S22, authentication terminal 10 has switch 16 disconnect first communication I/F 150 from battery 140. Power feed to first communication I/F 150 (radio wave transmitter 17) is thus stopped and first communication I/F 150 (radio wave transmitter 17) stops transmission of radio waves.

In step S24, authentication terminal 10 determines whether or not detection of the position of the user with the use of authentication terminal 10 ends. In one implementation, authentication terminal 10 determines that position detection ends in response to an instruction to power off authentication terminal 10. In another implementation, authentication terminal 10 determines that position detection ends when it receives input of an instruction to quit a position detection application.

When authentication terminal 10 determines that position detection ends (YES in step S24), the process in FIG. 5 ends, and otherwise (NO in step S24), the process returns to step S12.

In the first embodiment described above, authentication terminal 10 transmits a signal including a terminal ID only during a period for which user authentication is successful, and suspends transmission of the signal including the terminal ID during a period other than that period, that is, during a period other than the period for which user authentication is successful.

In other words, when the user puts off authentication terminal 10, biometric information cannot be obtained and user authentication is not successful either. Therefore, signal transmission is stopped.

When another user wears authentication terminal 10 as well, obtained biometric information is different from registered collation information. Therefore, user authentication is not successful and signal transmission is stopped.

Thus, erroneous position detection due to an authentication apparatus being distant from a true user or spoofing by another user can be prevented.

Second Embodiment

[1. Configuration of Position Detection System]

Figure 6:
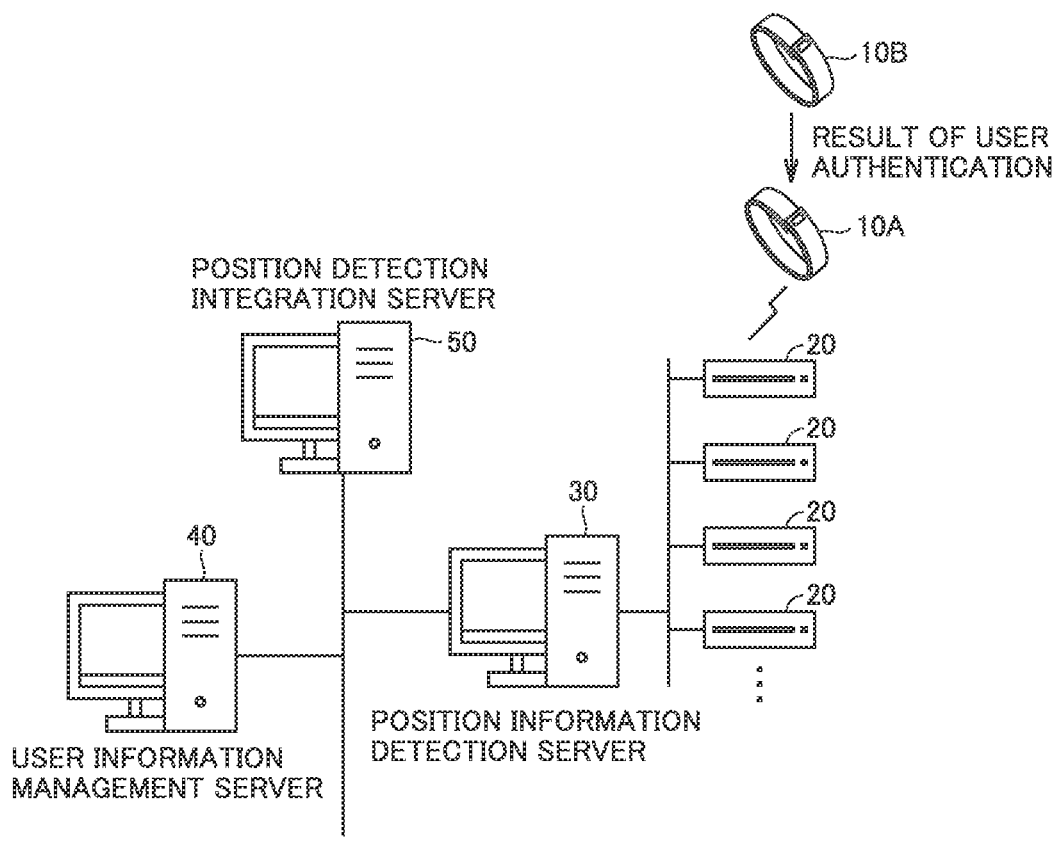
FIG. 6 is a diagram showing an exemplary configuration in a second embodiment of the position detection system.

FIG. 6 is a diagram showing an exemplary configuration in a second embodiment of the position detection system.

In the second embodiment of the position detection system, a user carries a communication terminal 10A and an authentication terminal 10B. For example, the user wears communication terminal 10A on one arm and wears authentication terminal 10B on the other arm. Communication terminal 10A functions as an RFID tag and transmits a signal including a terminal ID of communication terminal 10A. Authentication terminal 10B carries out user authentication and notifies communication terminal 10A of a result of user authentication.

In the second embodiment, communication terminal 10A represents an exemplary communication terminal and communication terminal 10A and authentication terminal 10B can perform the function of authentication terminal 10 in the first embodiment.

[2. Hardware Configuration]

Figure 7:
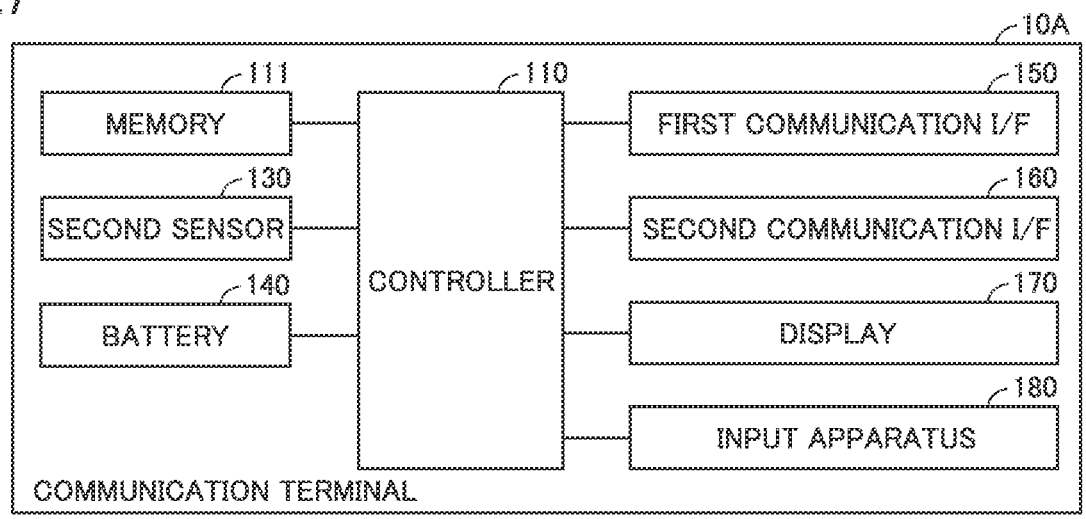
FIG. 7 is a diagram showing an exemplary hardware block of a communication terminal 10A.

FIG. 7 is a diagram showing an exemplary hardware block of communication terminal 10A. As compared with the hardware block of authentication terminal 10 shown in FIG. 3, communication terminal 10A does not include first sensor 120 but includes second sensor 130 because it does not have to carry out user authentication. Communication terminal 10A is otherwise similar in configuration to authentication terminal 10.

When detection of data for detecting whether or not the user is wearing authentication terminal 10B is required, second sensor 130 is used for detection of such data. In one implementation, authentication terminal 10B can determine whether or not it is worn by the user based on whether or not a temperature detected by second sensor 130 corresponds to a body temperature of a human. In this case, second sensor 130 can be implemented by a temperature sensor. In another implementation, authentication terminal 10B can determine whether or not it is worn by the user based on whether or not second sensor 130 detects heart rates corresponding to heart rates of a human. In this case, second sensor 130 is implemented by a heart rate sensor.

Authentication terminal 10B includes an element that carries out user authentication (for example, a processor such as a CPU and a sensor for obtaining biometric information or an input apparatus that accepts entry of a password) and an element (a communication interface) that notifies communication terminal 10A of a result of user authentication.

[3. Functional Configuration]

Figure 8:
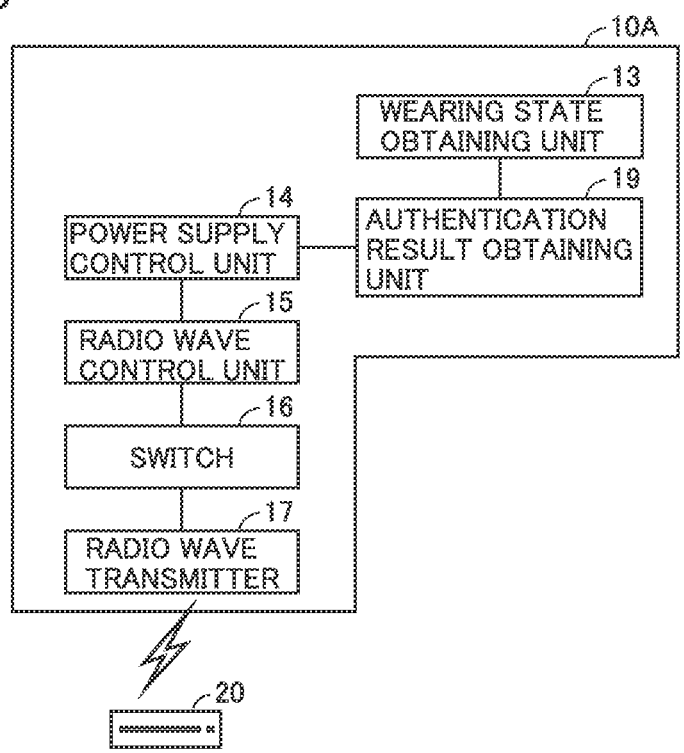
FIG. 8 is a diagram showing an exemplary functional configuration of communication terminal 10A.

FIG. 8 is a diagram showing an exemplary functional configuration of communication terminal 10A. As compared with the functional configuration of authentication terminal 10 shown in FIG. 4, communication terminal 10A does not include authentication unit 11, biometric information obtaining unit 12, and communication unit 18 but includes a wearing state obtaining unit 13 and an authentication result obtaining unit 19.

In authentication terminal 10B, wearing state obtaining unit 13 obtains data representing whether or not the user is wearing authentication terminal 10B and provides that data to authentication unit 11. Wearing state obtaining unit 13 is implemented by second sensor 130.

Authentication terminal 10B performs a function corresponding to authentication unit 11, biometric information obtaining unit 12, and communication unit 18, and further includes an element (a notification element) that notifies communication terminal 10A of a result of user authentication by authentication unit 11. Authentication unit 11 may carry out user authentication in response to a request from communication terminal 10A. The notification element is implemented, for example, by a communication interface provided in authentication terminal 10B.

In authentication terminal 10A, authentication result obtaining unit 19 obtains a result of user authentication from authentication terminal 10B. Authentication result obtaining unit 19 is implemented by first communication I/F 150 or second communication I/F 160.

[4. Type of Registered Information]

In the second embodiment, among types of information registered in authentication terminal 10 in the first embodiment, information included in a signal provided as an RFID tag is registered in communication terminal 10A and information to be used for user authentication is registered in authentication terminal 10B. In other words, in one implementation, a terminal ID managed in user information management server 40 (associated with a user name) is registered in communication terminal 10A and collation information to be used for user authentication is registered in authentication terminal 10B.

[5. Process Flow]

Figure 9:
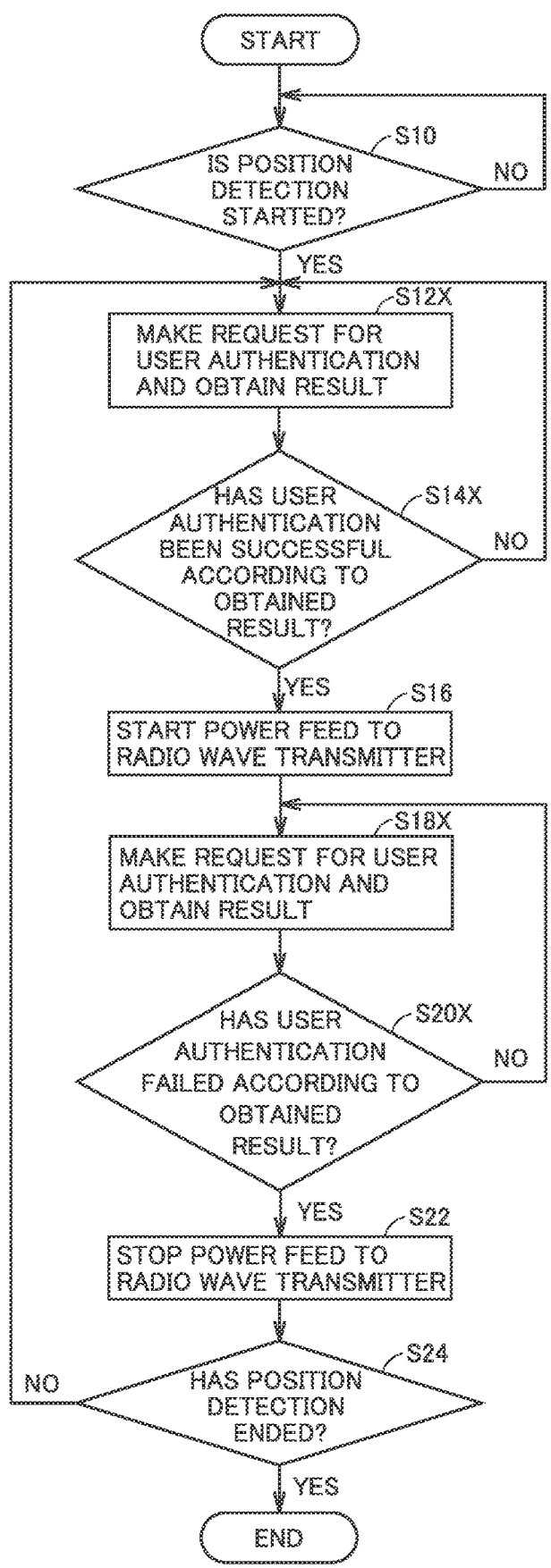
FIG. 9 is a flowchart of exemplary processing performed in communication terminal 10A.

FIG. 9 is a flowchart of exemplary processing performed in communication terminal 10A. Communication terminal 10A performs a process in FIG. 9, for example, by having a processor of controller 110 execute a given program.

The process in FIG. 9 is different from the process in FIG. 5 in contents of control in user authentication and determination as to a result of user authentication. More specifically, the process in FIG. 9 includes steps S12X, S14X, S18X, and S20X instead of steps S12, S14, S18, and S20 in the process in FIG. 5.

In step S12X, communication terminal 10A requests authentication terminal 10B to carry out user authentication and obtains from authentication terminal 10B, a result of user authentication carried out in response to the request.

In step S14X, communication terminal 10A determines whether or not the result obtained in step S12X indicates successful user authentication, and when the result indicates success (YES in step S14X), the process proceeds to step S16, and otherwise (NO in step S14X), the process returns to step S12X.

In step S18X, communication terminal 10A requests authentication terminal 10B to carry out user authentication as in step S12X, and obtains from authentication terminal 10B, a result of user authentication carried out in response to the request.

In step S20X, communication terminal 10A determines whether or not the result obtained in step S18X indicates failure in user authentication, and when the result indicates failure (YES in step S20X), the process proceeds to step S22, and otherwise (NO in step S20X), the process returns to step S18X.

In the second embodiment described above, communication terminal TOA transmits a signal including a terminal ID in response to success of user authentication by authentication terminal 10B, and stops transmission of the signal including the terminal ID in response to failure in user authentication by authentication terminal 10B.

Summary of Embodiments

[1]

In the first embodiment, authentication terminal 10 carries out user authentication. When authentication is successful, authentication terminal 10 has switch 16 connect first communication I/F 150 to battery 140, and when authentication fails, it has switch 16 disconnect first communication I/F 150 from battery 140. A state in which switch 16 has first communication I/F 150 connected to battery 140 represents an exemplary state (a first state) in which a signal including identification information is transmittable to an external apparatus. A state in which switch 16 has first communication I/F 150 disconnected from battery 140 represents an exemplary state (a second state) in which a signal including identification information is not transmitted to an external apparatus.

[2]

Though authentication terminal 10 can constantly carry out authentication while it is worn on a user's body, it may carry out user authentication at prescribed time intervals. In other words, in authentication terminal 10, user authentication is periodically carried out. Transmission of a signal in response to successful user authentication on one occasion may be maintained until next user authentication. When the authentication terminal is taken off from the user's body, however, maintained transmission of the signal in response to successful user authentication on one occasion may be canceled.

[3]

In the second embodiment, communication terminal 10A obtains a result of user authentication from authentication terminal 10B. When the result indicates successful user authentication, communication terminal 10A has switch 16 connect first communication I/F 150 to battery 140. When the result indicates failure in user authentication, communication terminal TOA has switch 16 disconnect first communication I/F 150 from battery 140.

[4]

Though authentication terminal 10 can constantly carry out authentication while it is worn on a user's body, it may obtain a result of user authentication at prescribed time intervals. In other words, in authentication terminal 10, a result of user authentication is periodically obtained. Transmission of a signal in response to successful user authentication on one occasion may be maintained until next user authentication. When the authentication terminal is taken off from the user's body, however, maintained transmission of the signal in response to successful user authentication on one occasion may be canceled.

[5]

Authentication terminal 10 (or communication terminal 10A) includes belt 112. Belt 112 represents an exemplary member for a user to put on authentication terminal 10 (or communication terminal 10A).

Authentication terminal 10 (or communication terminal 10A) is a watch type terminal device, belt 112 of which is attached to an arm of a user. Even when authentication terminal 10 (or communication terminal 10A) is a user wearable type terminal, a form thereof is not limited to the watch type. Authentication terminal 10 (or communication terminal 10A) may be a necklace type or sunglass type terminal. In an example of the necklace type, authentication terminal 10 (or communication terminal 10A) includes as the member, a string-like portion for putting the authentication terminal around the neck of the user. In an example of the sunglass type, authentication terminal 10 (or communication terminal 10A) includes as the member, an element for being worn on the face of the user.

[7]

Figure 10:
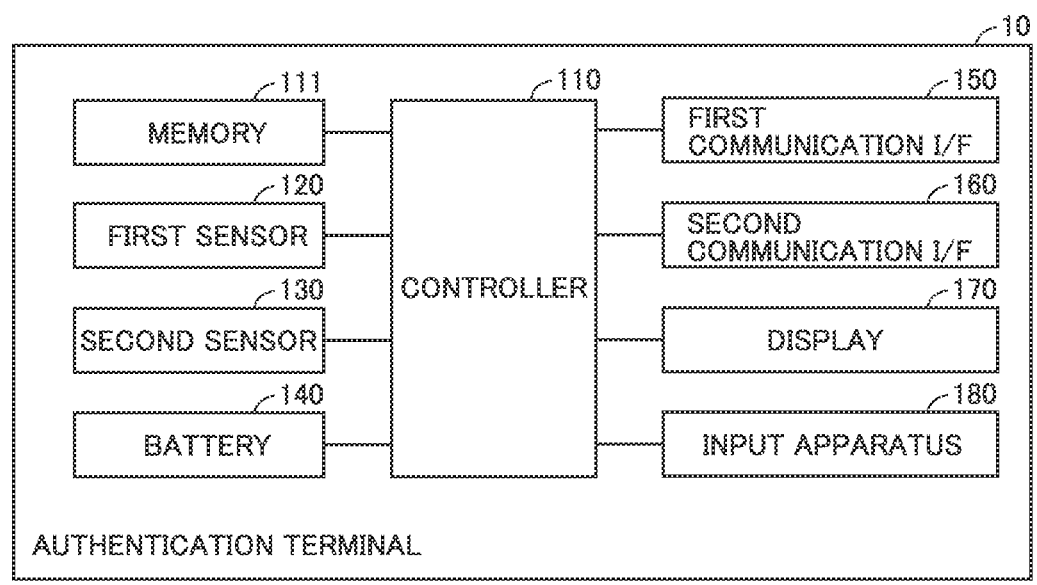
FIG. 10 is a diagram showing a modification of a hardware configuration of authentication terminal 10 in FIG. 3.
Figure 11:
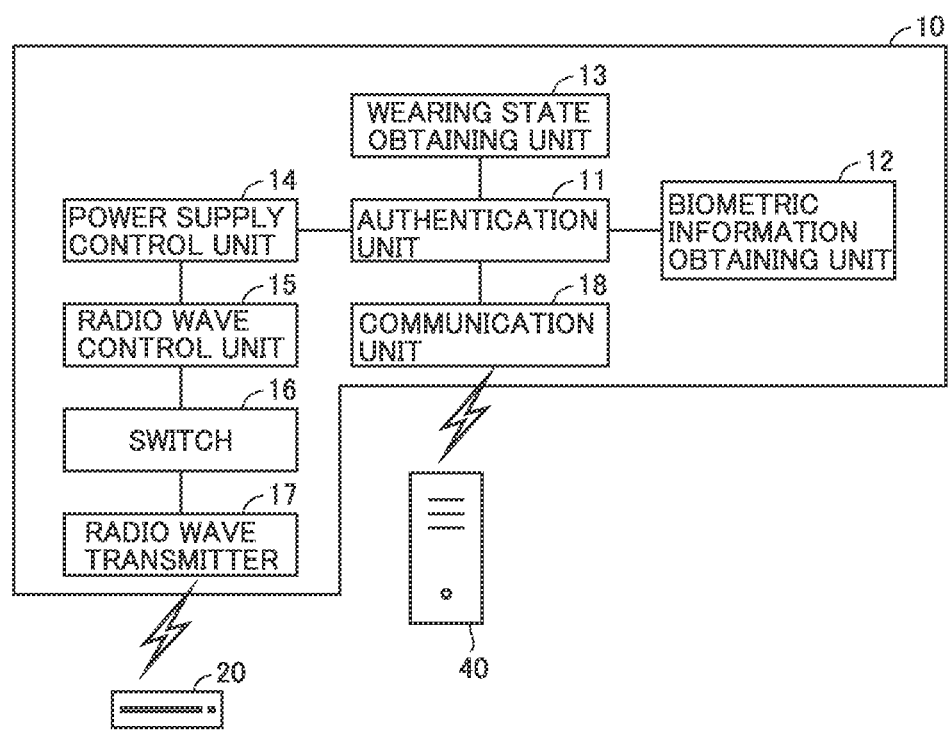
FIG. 11 is a diagram showing a modification of a functional configuration of authentication terminal 10 in FIG. 4.

FIG. 10 is a diagram showing a modification of a hardware configuration of authentication terminal 10 in FIG. 3. FIG. 11 is a diagram showing a modification of a functional configuration of authentication terminal 10 in FIG. 4.

As shown in FIG. 10, authentication terminal 10 (or communication terminal 10A) can also include a sensor that senses whether or not a user is wearing authentication terminal 10 (for example, a sensor (second sensor 130) that senses physical attachment and detachment or measures a body temperature of a user). At this time, as shown in FIG. 11, authentication terminal 10 includes wearing state obtaining unit 13.

In the example shown in FIGS. 10 and 11, authentication terminal 10 determines user authentication as being successful based on wearing continuation information obtained by second sensor 130 that represents a state in which the user continues to wear authentication terminal 10 and information on successful user authentication obtained by first sensor 120 at the time of start of wearing or at a certain time point during a period for which the authentication terminal is worn. A period during which the above information is both obtained is defined as a period during which user authentication is determined as being successful, and authentication terminal 10 can transmit a signal including identification information only during that period.

[8]

A sensor for determining whether or not the user is wearing authentication terminal 10 (or communication terminal 10A) may detect at least one of a body temperature and heart rates.

[9]

In authentication terminal 10 (or communication terminal 10A), when first communication I/F 150 is connected to battery 140, first communication I/F 150 (radio wave transmitter 17) transmits radio waves including a terminal ID. When first communication I/F 150 is disconnected from battery 140, power feed to first communication I/F 150 (radio wave transmitter 17) is stopped and first communication I/F 150 (radio wave transmitter 17) stops transmission of radio waves.

The terminal ID represents exemplary identification information associated with a user. In other words, in the position detection system, a terminal ID is associated with a user name in user information management server 40, and the user name is information for identifying each user. Therefore, in the position detection system, the terminal ID can be exemplary information associated with each user. In authentication terminal 10 (or communication terminal 10A), information of another type for identifying a user such as a user name or a user ID may be stored. Authentication terminal 10 (or communication terminal 10A) may transmit a signal including information of another type for detecting a position of a user, instead of or in addition to the terminal ID.

[10]

Authentication terminal 10 (or communication terminal 10A) switches between a state in which first communication I/F 150 is able to transmit radio waves and a state in which it is unable to transmit radio waves, by switching whether or not to supply electric power from battery 140 to first communication I/F 150. The state in which switch 16 has first communication I/F 150 connected to battery 140 represents an exemplary state in which first communication I/F 150 is able to transmit radio waves, and a state in which switch 16 has first communication I/F 150 disconnected from battery 140 represents an exemplary state in which first communication I/F 150 is unable to transmit radio waves. Authentication terminal 10 (or communication terminal 10A) may switch between the state in which first communication I/F 150 is able to transmit radio waves and the state in which it is unable to transmit radio waves, with a method other than switching whether or not to feed power from battery 140 to first communication I/F 150.

[11]

Though first communication I/F 150 is implemented, for example, by an RFID device that functions as an RFID tag, it is not limited thereto. First communication I/F 150 may be a beacon transmitter that transmits a beacon including a terminal ID or may be a WiFi module that transmits a signal including a terminal ID in conformity with WiFi specifications.

[12]

Authentication terminal 10 (or communication terminal 10A) may include switch 16 that switches between on and off of supply of electric power from battery 140 to first communication I/F 150 and may switch between on and off of transmission of a signal by radio wave transmitter 17 by control of on and off states by switch 16, Authentication terminal 10 (or communication terminal 10A) should only control on and off of transmission of a signal by radio wave transmitter 17 in accordance with a result of authentication, and switching between on and off of transmission of a signal by radio wave transmitter 17 is not limited to switching made by switch 16.

Switch 16 may turn off power feed to first communication I/F 150 (radio wave transmitter 17) not only when user authentication has failed but also when authentication terminal 10 (or communication terminal 10A) is not used for detection of a position of a user. For example, when controller 110 is instructed to stop detection of a position of a user through an operation onto input apparatus 180, it may have switch 16 disconnect first communication I/F 150 from battery 140. Waste of battery 140 can thus be suppressed.

[13]

In the first embodiment, authentication terminal 10 represents an exemplary first communication terminal, RFID reader 20 (20-A to 20-D) represents an exemplary second communication terminal, and position detection integration server 50 represents an exemplary server apparatus.

[14]

In the second embodiment, communication terminal 10A represents an exemplary first communication terminal, RFID reader 20 (20-A to 20-D) represents an exemplary second communication terminal, authentication terminal 10B represents an exemplary third communication terminal, and position detection integration server 50 represents an exemplary server apparatus.

Third Embodiment

[1. Overview]

The position detection system can include at least two authentication terminals 10. Authentication terminal 10 represents an exemplary "communication terminal" or "first communication terminal" and transmits a signal including information (a terminal ID) for identifying authentication terminal 10. In the position detection system, a terminal ID is associated with a user name in user information management server 40. The user name is information for identifying each user. Therefore, in the position detection system, the terminal ID can be concluded as exemplary identification information associated with a user.

Authentication terminal 10 is a watch type terminal device to be worn on an arm of a user. Authentication terminal 10 includes belt 112 for being attached to the arm of the user. Belt 112 represents an exemplary "attachment member." The user can thus wear authentication terminal 10 on the user's body. Though authentication terminal 10 is implemented by a wearable terminal in a third embodiment, the authentication terminal does not necessarily have to include a feature for being attached to the user's body. Authentication terminal 10 may be implemented by a terminal such as a smartphone in which an application program for performing a function as described herein is installed.

Authentication terminal 10 includes first sensor 120 (for example, a fingerprint sensor) used for user authentication and second sensor 130 (for example, a body temperature sensor) used for detection of continuation of wearing of authentication terminal 10 by the user. Details of a configuration of authentication terminal 10 can be described with reference to FIG. 3 or the like.

Authentication terminal 10 includes first communication interface 150 (the interface may also be denoted as "I/F"). First communication I/F 150 is implemented, for example, by an RFID device including a passive type RF tag In general, the passive type RF tag receives radio waves transmitted from RFID reader 20 to generate electric power and transmits radio waves by using electric power as motive power. First communication interface 150 receives radio waves transmitted from RFID reader 20 to generate electric power and transmits over radio waves, a signal including a terminal ID by using electric power as motive power. RFID reader 20 receives radio waves transmitted from first communication interface 150 and reads a terminal ID. Authentication terminal 10 includes such arrangement for being able to transmit a signal only when a true user is wearing authentication terminal 10 (corresponding to an "example in which user authentication is successful"). With such arrangement, RFID reader 20 can obtain a terminal ID only when user authentication is successful.

The position detection system can include at least two RFID readers 20. RFID reader 20 represents an exemplary "second communication terminal." When each RFID reader 20 receives a signal from authentication terminal 10, it transmits in association with each other, information (an RFID or the like that corresponds to "apparatus information") for identifying each RFID reader 20 and a terminal ID included in the signal to position information detection server 30. An RFID is stored in a memory of RFID reader 20. RFID reader 20 may further transmit information for specifying time of reception of the signal from authentication terminal 10 to position information detection server 30.

[2. Functional Configuration]

Figure 12:
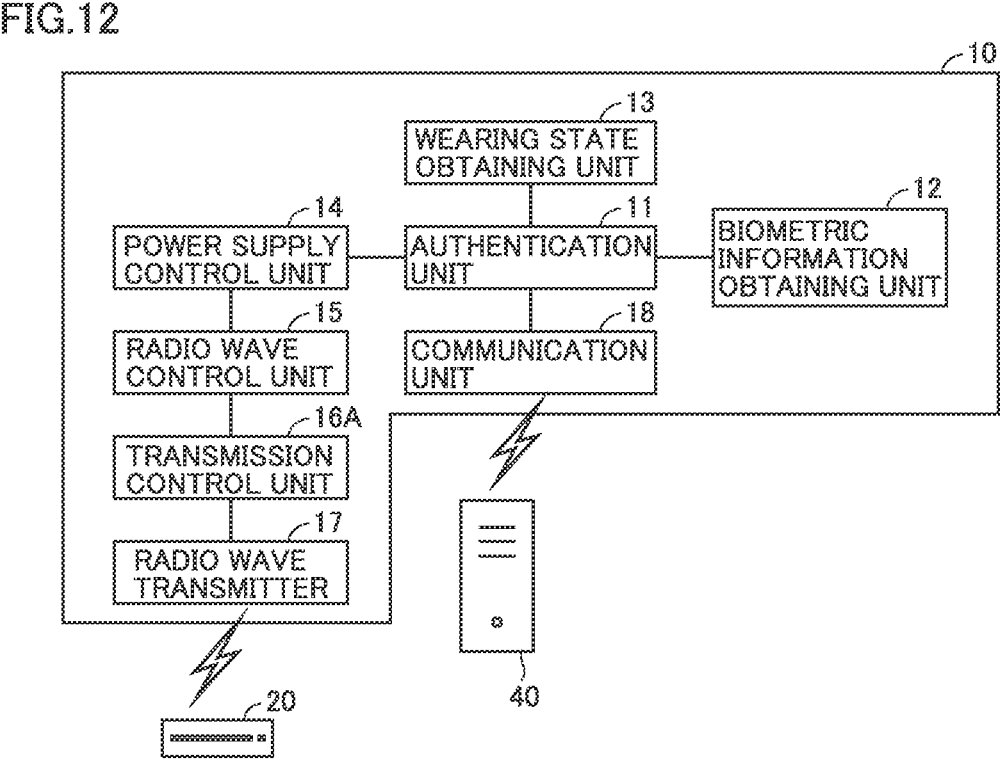
FIG. 12 is a diagram showing an exemplary functional configuration of authentication terminal 10 in a third embodiment.

FIG. 12 is a diagram showing an exemplary functional configuration of authentication terminal 10 in the third embodiment. As shown in FIG. 12, authentication terminal 10 includes a transmission control unit 16A.

Transmission control unit 16A controls transmission of a signal by authentication terminal 10 that functions as an RF tag. Transmission control unit 16A is implemented, for example, by an electric circuit included in controller 110. When user authentication is successful, transmission control unit 16A does not prevent transmission of a signal by first communication I/F 150, and when user authentication is not successful, it prevents transmission of a signal by first communication I/F 150.

Transmission control unit 16A controls transmission of a signal by authentication terminal 10, for example, by changing a distance between first communication I/F 150 and a blocking member which will be described later. In one implementation, when user authentication is successful, transmission control unit 16A increases a distance between first communication I/F 150 and the blocking member, and when user authentication is not successful, it decreases the distance between first communication I/F 150 and the blocking member.

In another example, transmission control unit 16A controls transmission of a signal by authentication terminal 10 by switching whether or not to supply a current to first communication I/F 150. In one implementation, when user authentication is successful, transmission control unit 16A does not allow supply of the current to first communication I/F 150, and when user authentication is not successful, it allows supply of the current to first communication I/F 150.

In the third embodiment, when radio wave transmitter 17 receives radio waves from RFID reader 20, it transmits a signal including a terminal ID registered in authentication terminal 10 over radio waves. The signal transmitted from radio wave transmitter 17 is received by RFID reader 20.

[3. Type of Registered Information]

An exemplary type of information registered in each element of the position detection system will be described.

(1) User Information Management Server 40

A user name, a terminal ID, and collation information are registered in user information management server 40 for each user.

In one implementation, in lending a terminal to each user, a manager of the position detection system registers a user name of each user and a terminal ID in user information management server 40 in association with each other. Each user applies for collation information with the manager. The manager further registers the collation information in user information management server 40, in association with the user name of each user.

(2) Authentication Terminal 10

A terminal ID and collation information are registered in authentication terminal 10.

In one implementation, a terminal ID is registered in authentication terminal 10 at the time of manufacturing thereof. In lending authentication terminal 10 to a user, a manager of the position detection system registers collation information applied for by the user in authentication terminal 10. Authentication terminal 10 in which collation information applied for by the user has been stored is lent to the user.

[4. First Example of Arrangement for Controlling Transmission of Signal by Authentication Terminal 10]

A first example of arrangement for controlling transmission of a signal by authentication terminal 10 will be described with reference to FIGS. 13 to 16. In the first example, transmission control unit 16A controls transmission of a signal by authentication terminal 10 by changing a distance between first communication I/F 150 and the blocking member.

Figure 13:
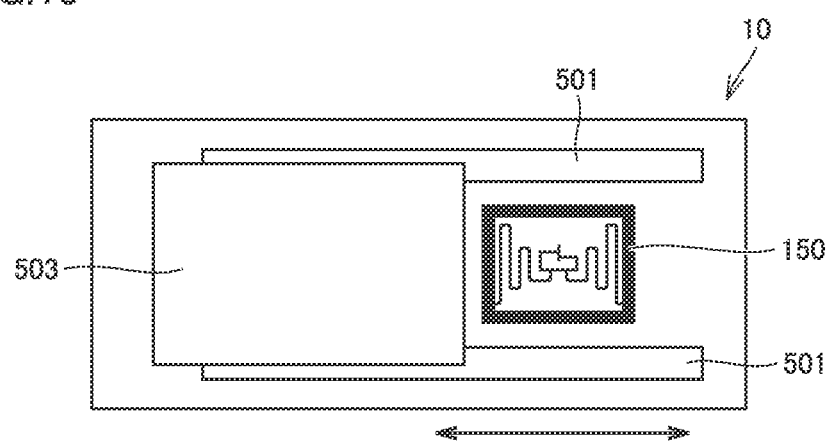
FIG. 13 is a diagram schematically showing a front view of a blocking member 503 and a first communication I/F 150.
Figure 14:
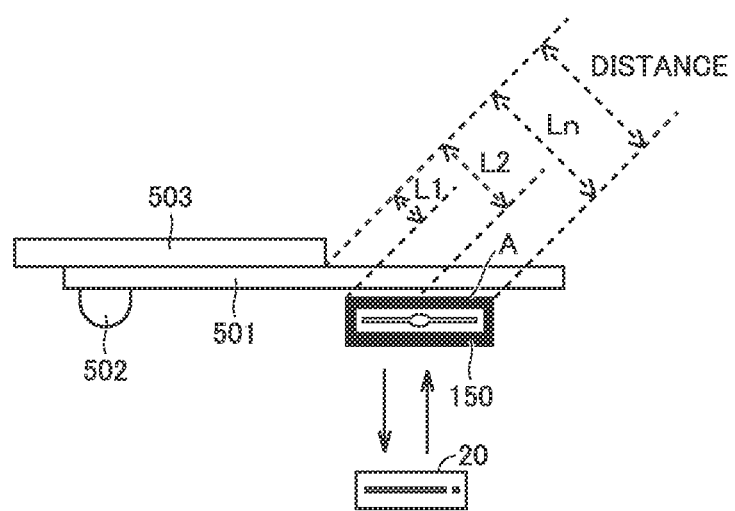
FIG. 14 is a diagram showing positional relation between blocking member 503 and first communication I/F 150 when user authentication is successful.
Figure 15:
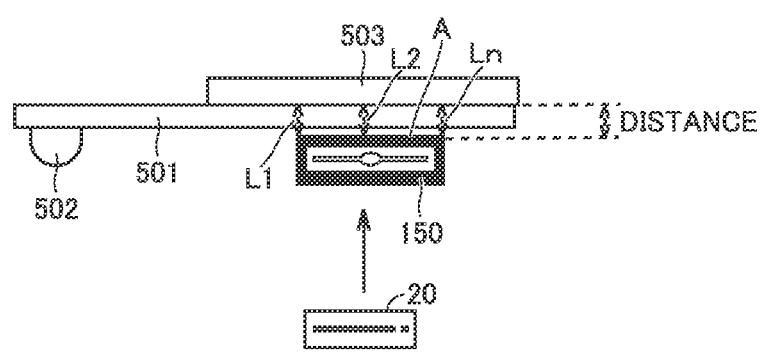
FIG. 15 is a diagram showing positional relation between blocking member 503 and first communication I/F 150 when user authentication is not successful.

FIG. 13 is a diagram schematically showing a front view of a blocking member 503 and first communication I/F 150. FIG. 14 is a diagram showing positional relation between blocking member 503 and first communication I/F 150 when user authentication is successful. FIG. 15 is a diagram showing positional relation between blocking member 503 and first communication I/F 150 when user authentication is not successful. FIGS. 14 and 15 schematically show a side view of blocking member 503 and first communication I/F 150.

Authentication terminal 10 includes first communication I/F 150, blocking member 503, and a mechanism for sliding blocking member 503. Blocking member 503 is a member that blocks reception and transmission of radio waves by first communication I/F 150. Blocking member 503 includes an element that absorbs and/or reflects radio waves. In one example, blocking member 503 is a member made of a metal. In another example, blocking member 503 is a member constituted of an element that absorbs radio waves and a container in which the element is accommodated. Liquid such as water represents an exemplary element that absorbs radio waves, and in such an example, blocking member 503 is implemented by liquid accommodated in a plastic container such as a PET bottle. A gel-like radio wave absorbing material represents another exemplary element that absorbs radio waves. The mechanism for sliding blocking member 503 includes a rail 501 and a motor 502. As motor 502 is driven, blocking member 503 moves along rail 501 in a direction shown with an arrow in FIG. 13. Transmission control unit 16A changes a distance between blocking member 503 and first communication I/F 150 by driving motor 502 to slide blocking member 503.

An exemplary value adopted as the distance between blocking member 503 and first communication I/F 150 is a value largest among shortest distances between blocking member 503 and points on an outer periphery of a surface (a surface A shown in FIGS. 14 and 15) opposed to blocking member 503, of surfaces of first communication I/F 150. In FIGS. 14 and 15, in an exemplary method of calculating a threshold value for the distance between blocking member 503 and first communication I/F 150, the shortest distances between n points on surface A of first communication I/F 150 and blocking member 503 are shown as distances L1, L2, . . . , and Ln (n being an integer equal to or larger than three). In the example in FIG. 14, distance Ln is longest among the shortest distances between the points on the outer periphery of surface A and blocking member 503. Therefore, distance Luis defined as the threshold value for the distance between blocking member 503 and first communication I/F 150. In the example in FIG. 15, values of distances L1, L2, . . . , and Ln are constant, and this constant value is defined as the distance between blocking member 503 and first communication I/F 150.

As shown in FIG. 14, when blocking member 503 and first communication I/F 150 are distant from each other, transmission of the signal by first communication I/F 150 is not blocked. When blocking member 503 and first communication I/F 150 are close as shown in FIG. 15, however, transmission of the signal by first communication I/F 150 is blocked. This is because, when blocking member 503 is close to first communication I/F 150, radio waves transmitted from RFID reader 20 or radio waves transmitted from first communication I/F 150 are blocked by blocking member 503.

In the example where blocking member 503 is made of a metal, when the distance between blocking member 503 and first communication I/F 150 becomes equal to or shorter than the threshold value, transmission of the signal by first communication I/F 150 is blocked. Specifically, when first communication I/F 150 is almost in contact with blocking member 503, an electric field component becomes zero at the surface of first communication I/F 150 in spite of transmission of radio waves from RFID reader 20. Therefore, first communication I/F 150 is unable to transmit a signal. Even in an example in which first communication I/F 150 is not in contact with blocking member 503, when the distance between blocking member 503 and first communication I/F 150 is equal to or shorter than the threshold value, radio waves (response waves) transmitted from RFID reader 20 and reflected at the surface of first communication I/F 150 are canceled by radio waves transmitted from RFID reader 20 and reflected at the surface of blocking member 503. Therefore, first communication I/F 150 is unable to transmit a signal. The threshold value is determined based on whether or not radio waves (response waves) transmitted from RFID reader 20 and reflected at the surface of first communication I/F 150 interfere with radio waves transmitted from RFID reader 20 and reflected at the surface of blocking member 503.

In an example where blocking member 503 includes an element that absorbs radio waves, when the distance between blocking member 503 and first communication I/F 150 becomes equal to or shorter than the threshold value, radio waves transmitted from RFID reader 20 are absorbed by blocking member 503. Therefore, first communication I/F 150 is unable to transmit a signal. The threshold value is determined based on whether or not radio waves transmitted from RFID reader 20 are absorbed by blocking member 503.

When user authentication is successful, authentication terminal 10 increases the distance between blocking member 503 and first communication I/F 150 to be longer than the threshold value such that transmission of the signal by first communication I/F 150 is not blocked. When user authentication is not successful, the authentication terminal decreases the distance between blocking member 503 and first communication I/F 150 to be equal to or shorter than the threshold value such that transmission of the signal from first communication I/F 150 is blocked. Authentication terminal 10 can thus transmit the signal only when user authentication is successful, and hence transmission of the terminal ID by authentication terminal 10 is limited to the occasion where user authentication is successful.

In the example shown in FIGS. 13 to 15, blocking member 503 is moved in a direction horizontal to first communication I/F 150 in order to change the distance between blocking member 503 and first communication I/F 150. In another example, blocking member 503 may be moved in a direction perpendicular to first communication I/F 150. Alternatively, instead of movement of blocking member 503 for changing the distance between blocking member 503 and first communication I/F 150, first communication I/F 150 may be moved. When first communication I/F 150 is moved in order to change the distance between blocking member 503 and first communication I/F 150, first communication I/F 150 is moved in the direction perpendicular or horizontal to blocking member 503. Alternatively, both of blocking member 503 and first communication I/F 150 may be moved in order to change the distance between blocking member 503 and first communication I/F 150.

Figure 16:
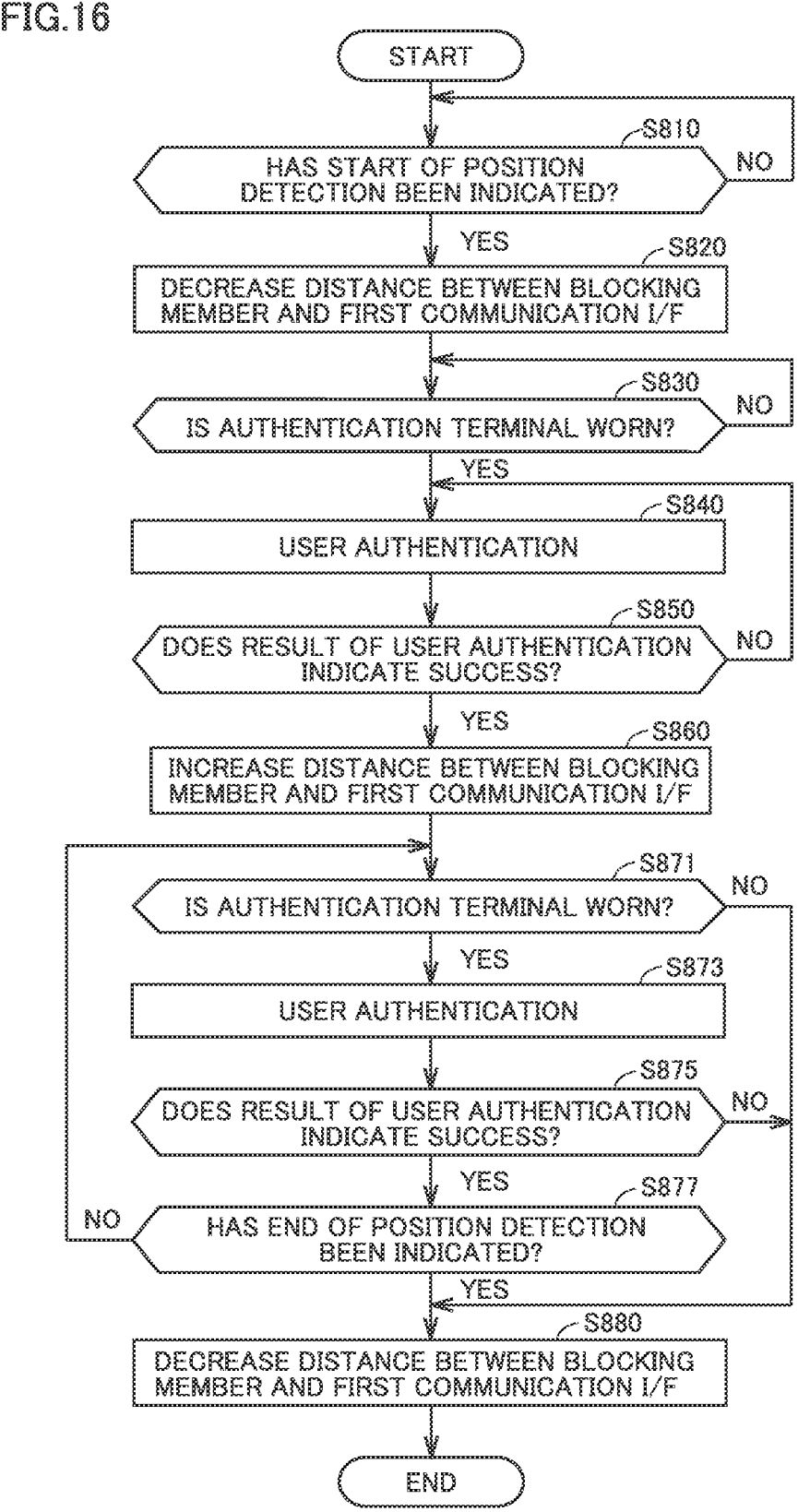
FIG. 16 is a flowchart showing processing performed in authentication terminal 10 in the third embodiment in which a first example is adopted.

FIG. 16 is a flowchart showing processing performed in authentication terminal 10 in the third embodiment in which a first example is adopted. Authentication terminal 10 performs a process in FIG. 16, for example, by having a processor of controller 110 execute a given program.

In step S810, authentication terminal 10 determines whether or not it has been instructed to start position detection. When authentication terminal 10 is configured to be used for position detection simultaneously with start of power on of authentication terminal 10, authentication terminal 10 determines that it has been instructed to start position detection in response to end of start-up processing at the time of power on. When authentication terminal 10 is configured to be used for position detection in response to a prescribed operation, authentication terminal 10 determines that it has been instructed to start position detection in response to the prescribed operation. When authentication terminal 10 determines that it has been instructed to start position detection (YES in step S810), the process proceeds to step S820, and otherwise (NO in step S810), the process remains in step S810.

In step S820, authentication terminal 10 drives motor 502 to decrease the distance between blocking member 503 and first communication I/F 150 to the threshold value or smaller. In one example, as a result of processing in step S820, blocking member 503 and first communication I/F 150 are in positional relation as shown in FIG. 15. First communication I/F 150 is thus unable to transmit a signal. When the distance between blocking member 503 and first communication I/F 150 has already been equal to or shorter than the threshold value, the process proceeds to step S830 with control in step S820 being skipped.

In step S830, authentication terminal 10 determines whether or not it is worn on a user's body. In one example, when second sensor 130 is a temperature sensor and a temperature range corresponding to the body temperature of a human is registered in advance in authentication terminal 10, in step S830, authentication terminal 10 has second sensor 130 detect a temperature and determines whether or not the temperature detected by second sensor 130 is within the registered temperature range. When the temperature detected by second sensor 130 is within the range, authentication terminal 10 determines that it is worn by the user, and when the temperature detected by second sensor 130 is out of the range, it determines that it is not worn by the user. When authentication terminal 10 determines that it is worn on the user's body (YES in step S830), the process proceeds to step S840, and otherwise (NO in step S830), the process remains in step S830.

In step S840, authentication terminal 10 carries out user authentication. In one example, when biometric information (for example, heart rates) is used for user authentication, in step S840, authentication terminal 10 detects heart rates as information for authentication by means of first sensor 120 (for example, a heart rate sensor) and checks the heart rates against the heart rate pattern registered as collation information.

In step S850, authentication terminal 10 determines whether or not a result of authentication in step S840 indicates success. Determination as YES in step S850 corresponds to an "example where user authentication is successful." When a result of authentication in step S840 indicates success (YES in step S850), the process proceeds to step S860, and otherwise (NO in step S850), the process returns to step S840.

In step S860, authentication terminal 10 drives motor 502 to increase the distance between blocking member 503 and first communication I/F 150 to be longer than the threshold value. In one example, as a result of processing in step S860, blocking member 503 and first communication I/F 150 are in positional relation as shown in FIG. 14. First communication I/F 150 is thus able to transmit a signal.

When a user carrying authentication terminal 10 is located in area AR (FIG. 2) in the position detection system, RFID reader 20 located in the vicinity of the user (any of RFID readers 20-A to 20-D in FIG. 2) receives the signal transmitted from authentication terminal 10.

In step S871, authentication terminal 10 determines whether or not it is worn on the user's body. Processing in step S871 is similar to that in step S830. Determination as NO in step S871 represents an "example in which user authentication is not successful." When authentication terminal 10 determines that it is worn on the user's body (YES in step S871), the process proceeds to step S873, and otherwise (NO in step S871), the process proceeds to step S880.

In step S873, authentication terminal 10 carries out user authentication. Processing in step S873 is similar to that in step S840.

In step S875, authentication terminal 10 determines whether or not a result of authentication in step S873 indicates success. Determination as NO in step S875 represents an "example where user authentication is not successful." When authentication terminal 10 determines a result of authentication in step S873 as indicating success (YES in step S875), the process proceeds to step S877, and otherwise (NO in step S875), the process proceeds to step S880.

In step S877, authentication terminal 10 determines whether or not it has been instructed to quit position detection. In one example, when authentication terminal 10 is instructed to turn off power, it determines that it has been instructed to quit position detection. When an instruction to quit an application for position detection is given to authentication terminal 10, it may determine that it has been instructed to quit position detection. Determination as YES in step S877 represents an "example where user authentication is not successful." When authentication terminal 10 determines that it has been instructed to quit position detection (YES in step S877), the process proceeds to step S880, and otherwise (NO in step S877), the process returns to step S871.

In step S880, authentication terminal 10 drives motor 502 to decrease the distance between blocking member 503 and first communication I/F 150 to be equal to or shorter than the threshold value. Processing in step S880 is similar to that in step S820. As a result of processing in step S880, first communication I/F 150 is no longer able to transmit a signal.

After step S880, authentication terminal 10 quits the process in FIG. 16.

[5. Second Example of Arrangement for Controlling Transmission of Signal by Authentication Terminal 10]

A second example of arrangement for controlling transmission of a signal by authentication terminal 10 will be described with reference to FIGS. 17 to 19. In the second example, transmission control unit 16A controls transmission of a signal by authentication terminal 10 by switching whether or not to supply a current to first communication I/F 150.

Figure 17:
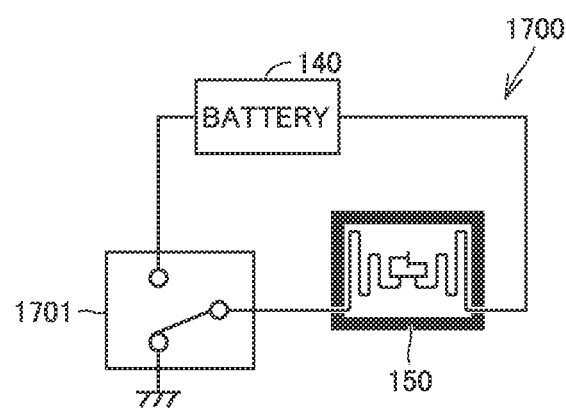
FIG. 17 is a diagram showing an example where user authentication is successful.
Figure 18:
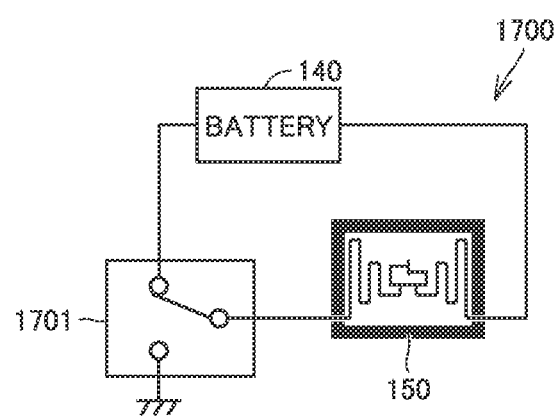
FIG. 18 is a diagram showing an example where user authentication is not successful.

FIG. 17 is a diagram showing an example where user authentication is successful. FIG. 18 is a diagram showing an example where user authentication is not successful. Authentication terminal 10 includes an electric circuit 1700. Electric circuit 1700 represents an exemplary mechanism that supplies a current to first communication I/F 150. Electric circuit 1700 includes first communication I/F 150, battery 140, and a switch 1701. Transmission control unit 16A controls switch 1701 to open or close so as to switch between a state in which a current is supplied to first communication I/F 150 and a state in which a current is not supplied to first communication I/F 150.

When user authentication is successful as shown in FIG. 17, switch 1701 is opened such that no current is supplied to first communication I/F 150. When user authentication is not successful as shown in FIG. 18, switch 1701 is closed such that a current is supplied to first communication I/F 150.

When the current is supplied to first communication I/F 150, radio waves are generated and generated radio waves cancel radio waves transmitted from RFID reader 20 or radio waves transmitted from first communication I/F 150. Therefore, first communication I/F 150 is unable to transmit a signal. When no current is supplied to first communication I/F 150, radio waves that interfere radio waves transmitted from RFID reader 20 or radio waves transmitted from first communication I/F 150 are not generated. Therefore, first communication I/F 150 is able to transmit a signal.

When user authentication is successful, authentication terminal 10 stops supply of a current to first communication I/F 150 such that transmission of a signal by first communication I/F 150 is not interfered. When user authentication is not successful, the authentication terminal allows supply of a current to first communication I/F 150 such that transmission of the signal by first communication I/F 150 is interfered. Authentication terminal 10 can thus transmit a signal only when user authentication is successful. Therefore, authentication terminal 10 transmits a terminal ID only when user authentication is successful.

Figure 19:
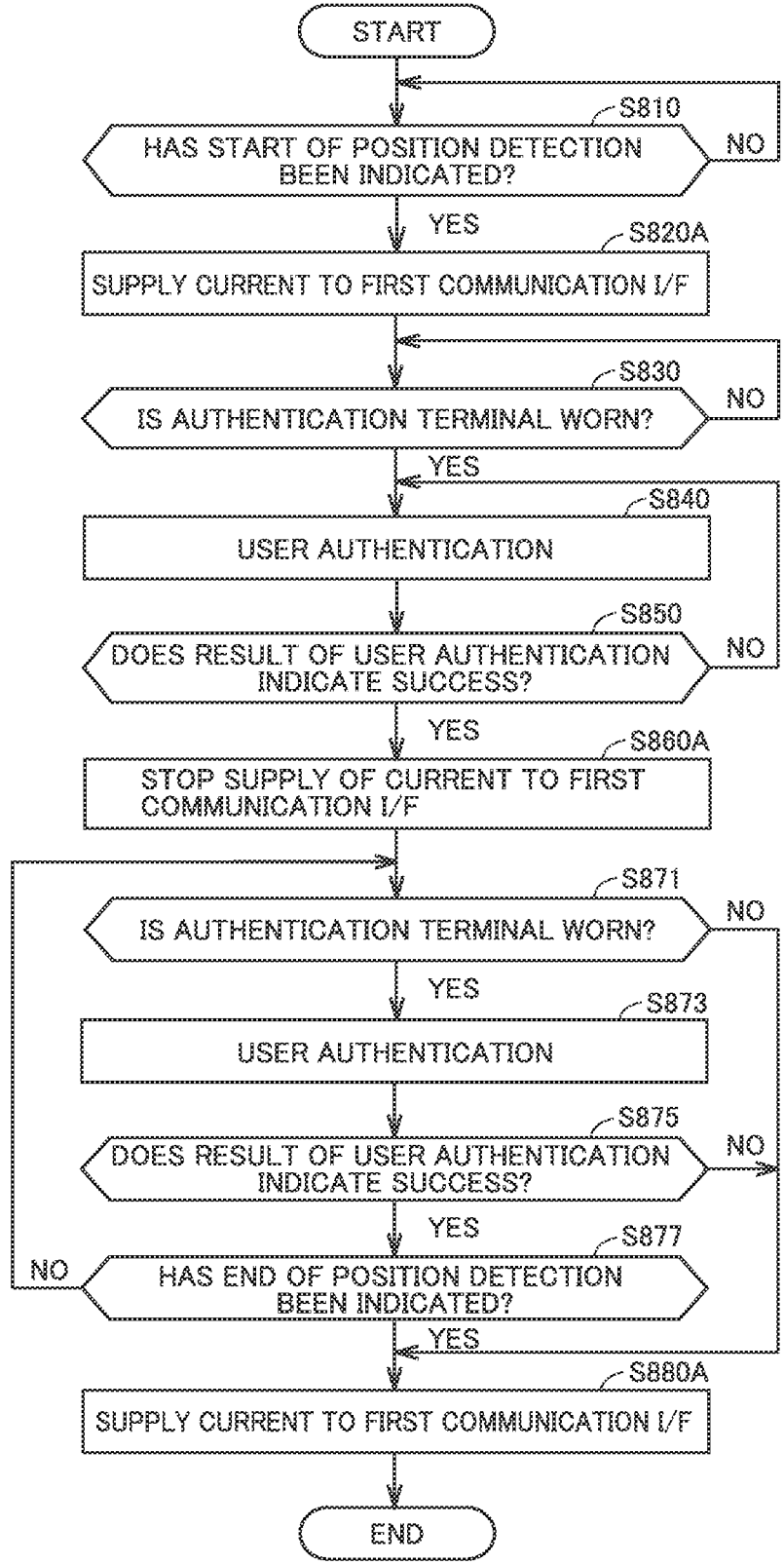
FIG. 19 is a flowchart showing processing performed in authentication terminal 10 in the third embodiment where a second example is adopted.

FIG. 19 is a flowchart showing processing performed in authentication terminal 10 in the third embodiment where the second example is adopted. Authentication terminal 10 performs a process in FIG. 19, for example, by having a processor of controller 110 execute a given program. The process in FIG. 19 is different from the process in FIG. 16 in contents of control for controlling transmission of a signal by authentication terminal 10. More specifically, the process in FIG. 19 includes steps S820A, S860A, and S880A instead of steps S820, S860, and S880 in the process in FIG. 16.

In step S820A, authentication terminal 10 closes switch 1701 to supply a current to first communication I/F 150. First communication I/F 150 is thus unable to transmit a signal.

In step S860A, authentication terminal 10 opens switch 1701 to stop supply of the current to first communication I/F 150. First communication I/F 150 is thus able to transmit a signal.

In step S880A, authentication terminal 10 closes switch 1701 to supply a current to first communication I/F 150. Processing in step S880A is similar to that in step S820A. As a result of processing in step S880A, first communication I/F 150 is unable to transmit a signal.

In the third embodiment described above, authentication terminal 10 carries out user authentication on condition that authentication terminal 10 is worn on the user's body, and only when user authentication is successful, it can transmit a signal including a terminal ID. When authentication terminal 10 fails in user authentication, when it is taken off from the user's body, or when it is instructed to quit position detection, it is unable to transmit a signal including a terminal ID.

Therefore, when the user puts off authentication terminal 10, transmission of the signal is stopped.

When another user wears authentication terminal 10, obtained biometric information is different from registered collation information. Therefore, user authentication is not successful and transmission of the signal is consequently stopped.

According to such arrangement, erroneous position detection due to the authentication terminal being distant from a true user or spoofing by another user can be prevented.

Fourth Embodiment

[1. Configuration of Position Detection System]

Figure 20:
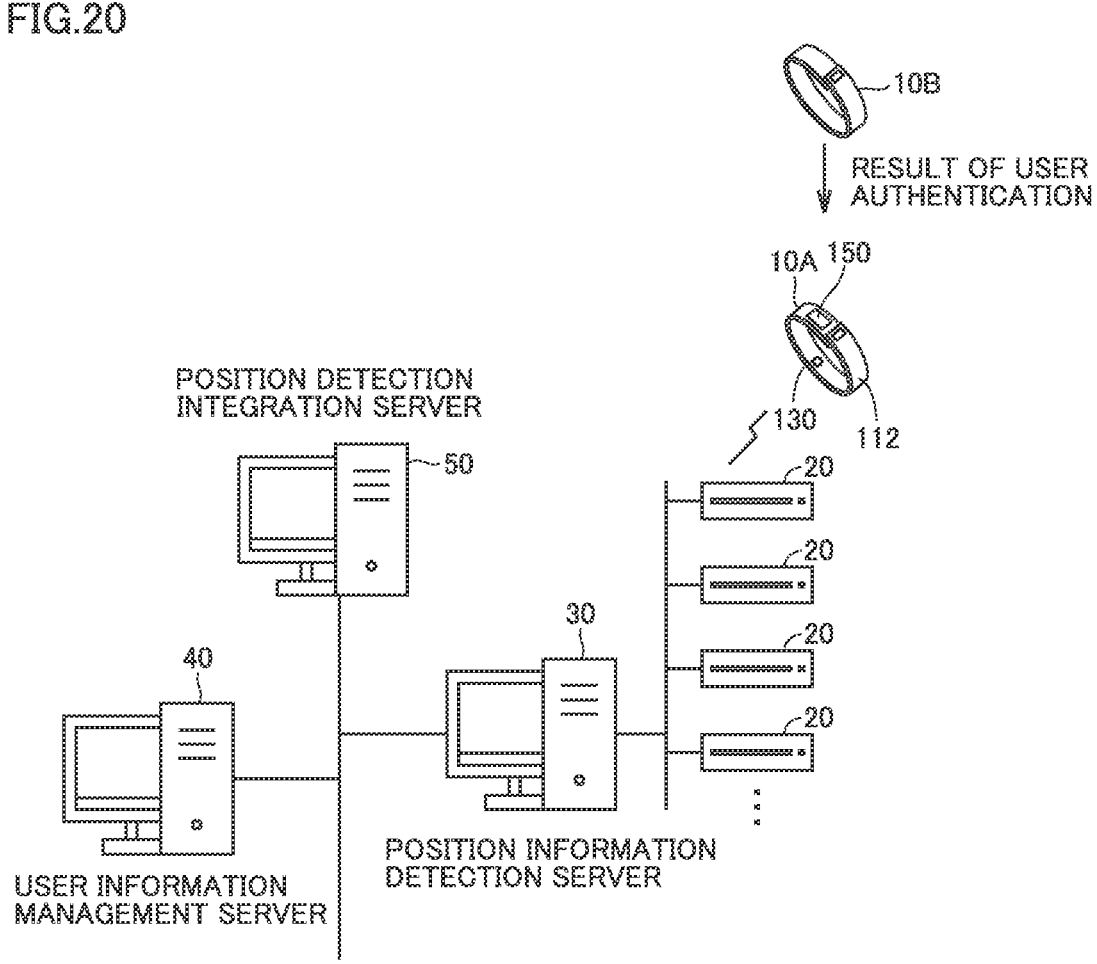
FIG. 20 is a diagram showing an exemplary configuration in a fourth embodiment of the position detection system.

FIG. 20 is a diagram showing an exemplary configuration in a fourth embodiment of the position detection system.

In the fourth embodiment of the position detection system, a user carries communication terminal 10A and authentication terminal 10B. For example, the user wears communication terminal 10A on one arm and wears authentication terminal 10B on the other arm. Communication terminal 10A represents an exemplary "communication terminal" or "first communication terminal" and transmits a signal including information (a terminal ID) for identifying communication terminal 10A. Authentication terminal 10B represents an exemplary "third communication terminal." Authentication terminal 10B carries out user authentication and notifies communication terminal 10A of a result of user authentication. In other words, communication terminal 10A and authentication terminal 10B can perform a function of authentication terminal 10 in the third embodiment. RFID reader 20 represents an exemplary "second communication terminal" and position detection integration server 50 represents an exemplary "server apparatus."

[2. Hardware Configuration]

Figure 21:
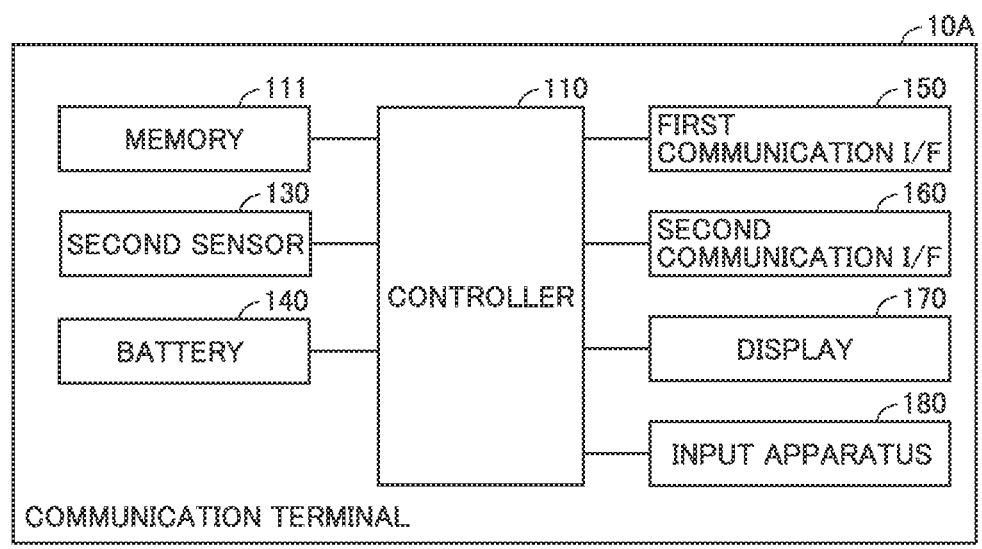
FIG. 21 is a diagram showing an exemplary hardware block of communication terminal 10A in the fourth embodiment.

FIG. 21 is a diagram showing an exemplary hardware block of communication terminal 10A in the fourth embodiment. As compared with the hardware block of authentication terminal 10 shown in FIG. 3, communication terminal 10A does not include first sensor 120 because it does not have to carry out user authentication. Communication terminal 10A is otherwise similar in configuration to authentication terminal 10.

Authentication terminal 10B includes an element that carries out user authentication (for example, a processor such as a CPU and a sensor for obtaining biometric information or an input apparatus that accepts entry of a password) and an element (a communication interface) that notifies communication terminal 10A of a result of user authentication.

[3. Functional Configuration]

Figure 22:
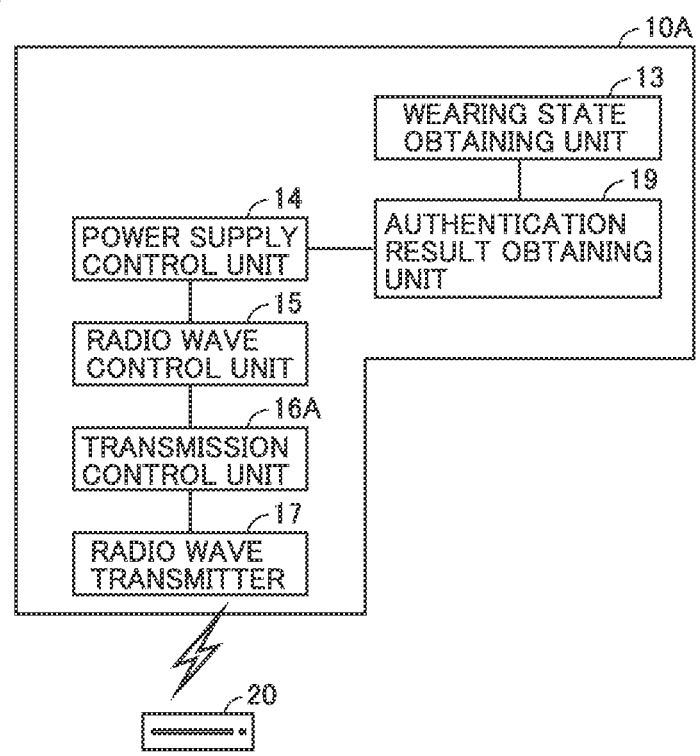
FIG. 22 is a diagram showing an exemplary functional configuration of communication terminal 10A in the fourth embodiment.

FIG. 22 is a diagram showing an exemplary functional configuration of communication terminal 10A in the fourth embodiment. As compared with the functional configuration of authentication terminal 10 shown in FIG. 12, communication terminal 10A does not include authentication unit 11, biometric information obtaining unit 12, and communication unit 18 but includes authentication result obtaining unit 19.

Authentication result obtaining unit 19 obtains a result of user authentication from authentication terminal 10B. Authentication result obtaining unit 19 is implemented by first communication I/F 150 or second communication I/F 160.

Authentication terminal 10B performs a function corresponding to authentication unit 11, biometric information obtaining unit 12, and communication unit 18 and further includes an element (a notification element) that notifies communication terminal 10A of a result of user authentication by authentication unit 11. Authentication unit 11 may carry out user authentication in response to a request from communication terminal 10A. The notification element is implemented, for example, by a communication interface provided in authentication terminal 10B.

[4. Type of Registered Information]

In the fourth embodiment, among types of information registered in authentication terminal 10 in the third embodiment, information included in a signal provided as an RF tag is registered in communication terminal 10A and information to be used for user authentication is registered in authentication terminal 10B. In other words, in one implementation, a terminal ID managed in user information management server 40 (associated with a user name) is registered in communication terminal 10A and collation information to be used for user authentication is registered in authentication terminal 10B.

[5. Process Flow]

Figure 23:
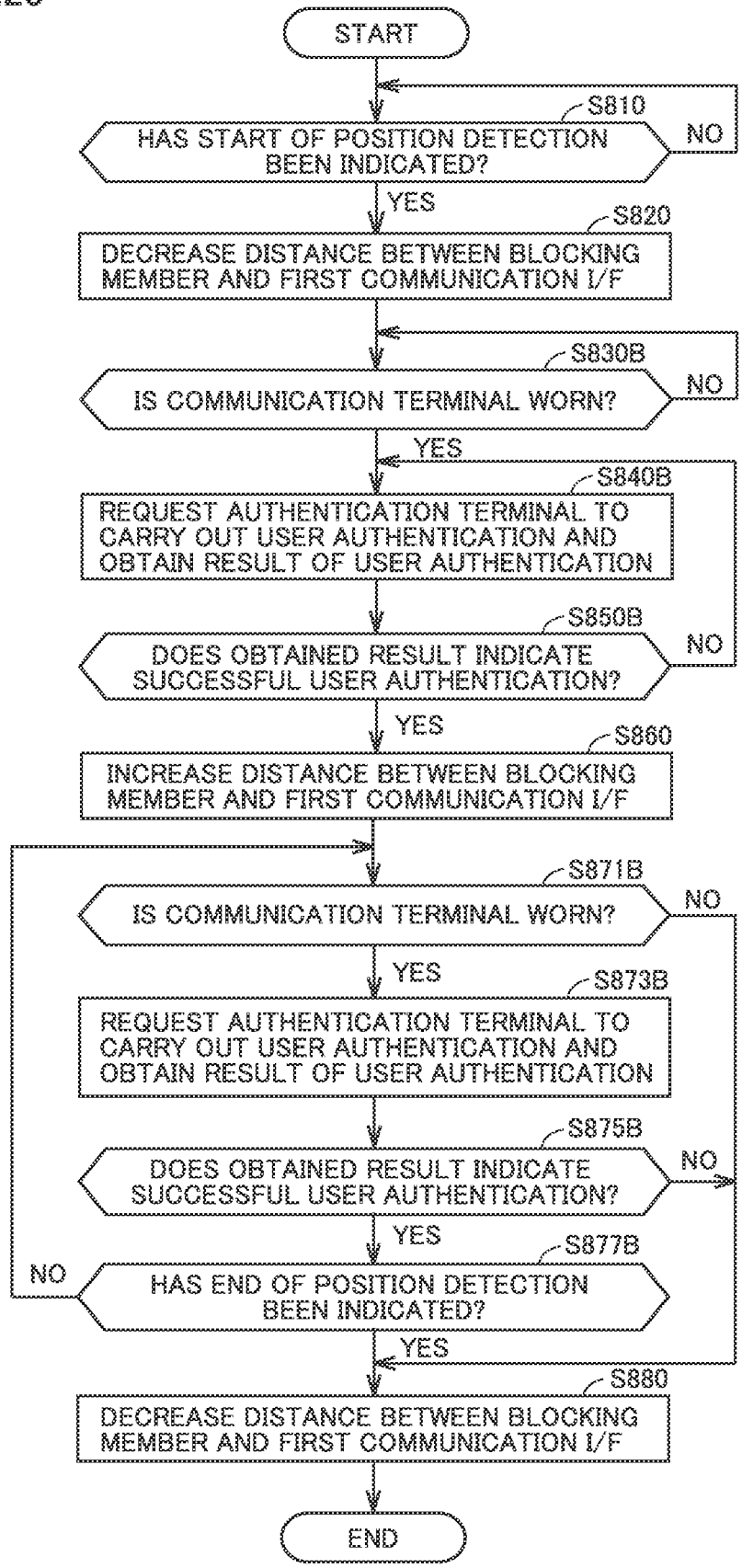
FIG. 23 is a flowchart showing processing performed in communication terminal 10A in the fourth embodiment where the first example is adopted.

Communication terminal 10A can adopt the first example or the second example described in the third embodiment as arrangement for controlling transmission of a signal. FIG. 23 is a flowchart showing processing performed in communication terminal 10A in the fourth embodiment where the first example is adopted. Communication terminal 10A performs a process in FIG. 23, for example, by having a processor of controller 110 execute a given program.

The process in FIG. 23 is different from the process in FIG. 16 in contents of control associated with user authentication. More specifically, the process in FIG. 23 includes steps S830B, S840B, S850B, S871B, S873B, S875B, and S877B instead of steps S830, S840, S850, S871, S873, S875, and S877 in the process in FIG. 16.

In step S830B, communication terminal 10A determines whether or not it is worn on the user's body. When communication terminal 10A determines that it is worn on the user's body (YES in step S830B), the process proceeds to step S840B, and otherwise (NO in step S830B), the process remains in step S830B.

In step S8401B, communication terminal 10A requests authentication terminal 10B to carry out user authentication and obtains from authentication terminal 10B, a result of user authentication carried out in response to the request.

In step S850B, communication terminal 10A determines whether or not the result obtained in step S840B indicates successful user authentication. Determination as YES in step S850B corresponds to an "example where user authentication is successful." When the result obtained in step S840B indicates successful user authentication (YES in step S850B), the process proceeds to step S860, and otherwise (NO in step S850B), the process returns to step S840B.

In step S871B, communication terminal 10A determines whether or not it is worn on the user's body. Processing in step S871B is similar to that in step S830B. Determination as NO in step S871B represents an "example where user authentication is not successful." When communication terminal 10A determines that it is worn on the user's body (YES in step S871B), the process proceeds to step S873B, and otherwise (NO in step S871B), the process proceeds to step S880.

In step S873B, communication terminal 10A requests authentication terminal 10B to carry out user authentication and obtains from authentication terminal 10B, a result of user authentication carried out in response to the request. Processing in step S873B is similar to that in step S8401B.

In step S875B, communication terminal 10A determines whether or not the result obtained in step S873B indicates successful user authentication. Determination as NO in step S875B represents an "example where user authentication is not successful." When communication terminal 10A determines the result obtained in step S873B as indicating successful user authentication (YES in step S875B), the process proceeds to step S877B, and otherwise (NO in step S875B), the process proceeds to step S880.

In step S877B, communication terminal 10A determines whether or not it has been instructed to quit position detection. In one example, when communication terminal 10A is instructed to turn off power, it determines that it has been instructed to quit position detection. When an instruction to quit an application for position detection is given to communication terminal 10A, it may determine that it has been instructed to quit position detection. Determination as YES in step S877B represents an example where "user authentication is not successful." When communication terminal 10A determines that it has been instructed to quit position detection (YES in step S877B), the process proceeds to step S880, and otherwise (NO in step S877B), the process returns to step S871B.

Figure 24:
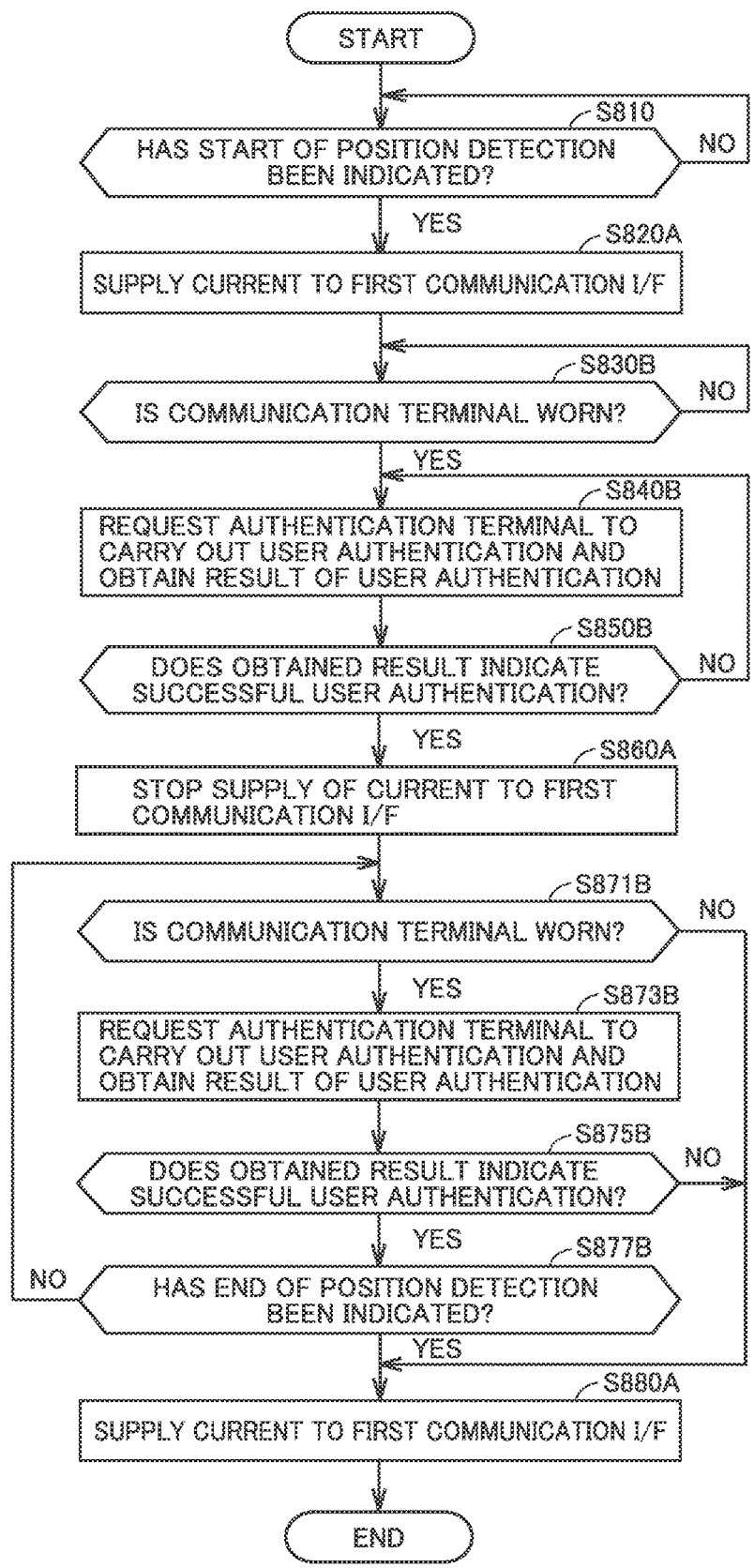
FIG. 24 is a flowchart showing processing performed in communication terminal 10A in the fourth embodiment where the second example is adopted.

FIG. 24 is a flowchart showing processing performed in communication terminal 10A in the fourth embodiment where the second example is adopted. Communication terminal 10A performs a process in FIG. 24, for example, by having a processor of controller 110 execute a given program.

The process in FIG. 24 is different from the process in FIG. 19 in contents of control associated with user authentication. More specifically, the process in FIG. 24 includes steps S830B, S840B, S850B, S871B, S873B, S875B, and S877B instead of steps S830, S840, S850, S871, S873, S875, and S877 in the process in FIG. 19.

In the fourth embodiment described above, communication terminal 10A obtains a result of user authentication from authentication terminal 10B on condition that communication terminal 10A is worn on the user's body, and it can transmit a signal including a terminal ID only when the obtained result indicates successful user authentication. When the obtained result indicates failure in user authentication, when communication terminal 10A is taken off from the user's body, or when communication terminal 10A is instructed to quit position detection, communication terminal 10A is unable to transmit a signal including a terminal ID. Consequently, erroneous position detection due to the communication terminal being distant from a true user or another user disguising himself/herself as the true user can be prevented.

MODIFICATION

Some of possible modifications will be shown below.

Though authentication terminal 10 (or communication terminal 10A) is a watch type terminal device including belt 112 to be attached to an arm of a user, it is not limited to the watch type so long as it is a user wearable type terminal. Authentication terminal 10 (or communication terminal 10A) may be a necklace type or a sunglass type. In an example of the necklace type, authentication terminal 10 (or communication terminal 10A) includes as the "attachment member," a string-like portion for putting the authentication terminal around the neck of the user. In an example of the sunglass type, authentication terminal 10 (or communication terminal 10A) includes as the "attachment member," an element for being worn on the face of the user. Alternatively, authentication terminal 10 (or communication terminal 10A) may be a terminal dangled from belongings or clothing of a user (a key holder type terminal). In an example of the key holder type, authentication terminal 10 (or communication terminal 10A) includes as the "attachment member," a hook for dangling from belongings or clothing of the user.

Though a terminal ID is stored as identification information associated with a user, limitation thereto is not intended. In authentication terminal 10 (or communication terminal 10A), identification information of another type associated with a user such as a user name or a user ID may be stored. Authentication terminal 10 (or communication terminal 10A) may transmit a signal including identification information of another type for detecting a position of a user, instead of or in addition to a terminal ID.

Though first communication I/F 150 is implemented, for example, by an RFID device including a passive type RF tag in the embodiments, it is not limited thereto. First communication I/F 150 may be implemented by an RFID device including a semi-passive type RF tag or an RFID device including an active type RF tag. Alternatively, first communication I/F 150 may be a beacon transmitter that transmits a beacon including a terminal ID or may be a WiFi module that transmits a signal including a terminal ID in conformity with WiFi specifications.

Although embodiments of the present invention have been described and illustrated in detail, the disclosed embodiments are made for the purposes of illustration and example only and not limitation. The scope of the present invention should be interpreted by terms of the appended claims.

What is claimed is:

1. A communication terminal comprising:
a memory configured to store identification information associated with a user;
a controller configured to authenticate the user;
a communication interface configured to transmit a signal over radio waves including the identification information; and
wherein the controller is configured to:
set, when authentication of the user is successful, the communication terminal to a first state in which the signal is transmitted to an external apparatus;
set, when authentication of the user is not successful, the communication terminal to a second state in which the signal is not transmitted to the external apparatus;
prevent, when a distance between a blocking member and the communication interface is equal to or less than a threshold value, the transmission of the signal by the communication interface to the external apparatus; and
allow, when the distance between the blocking member and the communication interface is greater than the threshold value, the transmission of the signal by the communication interface.

2. The communication terminal according to claim 1, wherein
the controller is configured to switch between the first state and the second state by controlling transmission of the signal by the communication interface.

3. The communication terminal according to claim 1, wherein
the controller is configured to switch between the first state and the second state by controlling a mechanism that blocks the signal transmitted by the communication interface.

4. A communication terminal comprising:
a memory in which identification information associated with a user is stored;
a controller configured to obtain a result of authentication of the user from a device that carries out user authentication;
a communication interface that transmits a signal including the identification information and transmission of the signal by the communication interface includes transmission of the signal over radio waves,
the controller is configured to:
prevent transmission of the signal by the communication interface when authentication of the user is not successful, and
does not prevent transmission of the signal by the communication interface when authentication of the user is successful; and
a blocking member configured to block transmission and reception of radio waves by the communication interface,
prevention of transmission of the signal by the communication interface includes decrease in distance between the blocking member and the communication interface to a threshold value or smaller under control by the controller, and
absence of prevention of transmission of the signal by the communication interface includes increase in distance between the blocking member and the communication interface to a distance larger than the threshold value under control by the controller.

5. The communication terminal according to claim 4, wherein
the communication terminal is wearable on a body of the user, and
the controller is configured to obtain the result from the device when the communication terminal is taken off from the body of the user.

6. The communication terminal according to claim 1, further comprising a member for putting the communication terminal on a body of the user.

7. The communication terminal according to claim 6, wherein
the communication terminal is a watch type, necklace type, or sunglass type terminal.

8. The communication terminal according to claim 1, further comprising a sensor that measures biometric information of the user, wherein
the controller is configured to determine whether the communication terminal is worn on a body of the user based on a detection output from the sensor.

9. The communication terminal according to claim 8, wherein
the sensor is configured to detect at least one of a body temperature and a heart rate.

10. The communication terminal according to claim 1, wherein
the communication interface is configured to transmit the signal in the first state and stop transmission of the signal in the second state.

11. The communication terminal according to claim 1, wherein
the controller is configured to set the communication terminal to a state in which the communication interface is able to transmit the signal or a state in which the communication interface is unable to transmit the signal, by switching whether to supply electric power to the communication interface.

12. The communication terminal according to claim 1, further comprising a switch configured to switch between on and off of electric power supply from a power supply to the communication interface, wherein
the controller is configured to set a state in which the communication interface is able to transmit the signal or a state in which the communication interface is unable to transmit the signal, by switching between on and off of electric power supply by the switch.

13. The communication terminal according to claim 4, wherein
the controller is configured to determine that the user authentication is not successful when the user authentication has failed or when the communication terminal is taken off from a body of the user.

14. The communication terminal according to claim 4, wherein
the blocking member is a member made of a metal or a member that absorbs radio waves.

15. The communication terminal according to claim 4, wherein
prevention of transmission of the signal by the communication interface includes supply of a current to the communication interface under control by the controller, and
absence of prevention of transmission of the signal by the communication interface includes stop of supply of the current to the communication interface under control by the controller.

16. The communication terminal according to claim 1, wherein
the communication interface includes at least one of a radio frequency (RF) identifier (ID) device, a beacon emitter, and a WiFi module.

17. The communication terminal according to claim 16, wherein
the RFID device includes a passive type RF tag, a semi-passive type RF tag, or an active type RF tag.

18. The communication terminal according to claim 4, further comprising a member for putting the communication terminal on a body of the user.

19. The communication terminal according to claim 18, wherein
the communication terminal is a watch type, necklace type, or sunglass type terminal.

20. The communication terminal according to claim 4, further comprising a sensor configured to measure biometric information of the user, wherein
the controller is configured to determine whether the communication terminal is worn on a body of the user based on a detection output from the sensor.

21. The communication terminal according to claim 20, wherein
the sensor is configured to detect at least one of a body temperature and a heart rate.

22. The communication terminal according to claim 4, wherein
the communication interface is configured to transmit the signal when authentication of the user is successful and stop transmission of the signal when authentication of the user is not successful.

23. The communication terminal according to claim 4, wherein
the controller is configured to set the communication terminal to a state in which the communication interface is able to transmit the signal or a state in which the communication interface is unable to transmit the signal, by switching whether to supply electric power to the communication interface.

24. The communication terminal according to claim 4, further comprising a switch configured to switch between on and off of electric power supply from a power supply to the communication interface, wherein
the controller is configured to set a state in which the communication interface is able to transmit the signal or a state in which the communication interface is unable to transmit the signal, by switching between on and off of electric power supply by the switch.

25. The communication terminal according to claim 4, wherein
the communication interface includes at least one of a radio frequency (RF) identifier (ID) device, a beacon emitter, and a WiFi module.

26. The communication terminal according to claim 25, wherein
the RFID device includes a passive type RF tag, a semi-passive type RF tag, or an active type RF tag.

27. A position detection system comprising:
a first communication terminal;
a second communication terminal configured to communicate with the first communication terminal; and
a server apparatus, wherein
the first communication terminal includes
a first memory in which identification information associated with a user is stored,
a controller configured to perform authentication of the user, and
a communication interface configured to transmit a signal including the identification information,
the controller is configured to:
set, when authentication of the user is successful, the first communication terminal to a first state in which the signal is transmitted to the second communication terminal, and
set, when authentication of the user is not successful, the first communication terminal to a second state in which the signal is not transmitted to the second communication terminal, the second communication terminal includes a second memory in which apparatus information for identifying the second communication terminal is stored, the second communication terminal is configured to transmit the identification information and the apparatus information to the server apparatus in response to reception of the identification information from the first communication terminal, and the server apparatus is configured to specify that the user specified by the identification information is located at a location corresponding to the second communication terminal specified by the apparatus information in response to reception of the identification information and the apparatus information from the second communication terminal.

28. A position detection system comprising:

a first communication terminal;

a second communication terminal configured to communicate with the first communication terminal;

a third communication terminal configured to communicate with the first communication terminal; and a server apparatus, wherein the first communication terminal includes a first memory in which identification information associated with a user is stored, the third communication terminal is configured to perform user authentication, the first communication terminal includes
- a controller configured to obtain a result of the user authentication from the third communication terminal, and
- a communication interface configured to emit a signal including the identification information, the controller is configured to:
- prevent transmission of the signal by the communication interface when the user authentication is not successful, and
- does not prevent transmission of the signal by the communication interface when the user authentication is successful, the second communication terminal includes a second memory in which apparatus information for identifying the second communication terminal is stored, the second communication terminal is configured to transmit the identification information and the apparatus information to the server apparatus in response to reception of the identification information from the first communication terminal, and the server apparatus is configured to specify the user specified by the identification information is located at a location corresponding to the second communication terminal specified by the apparatus information in response to reception of the identification information and the apparatus information from the second communication terminal.

\* \* \* \* \*